United States Patent
Stokes et al.

(10) Patent No.: US 9,597,082 B2
(45) Date of Patent: Mar. 21, 2017

(54) METHOD AND APPARATUS FOR SEALING END-TO-END ANASTOMOSIS

(71) Applicant: Ethicon Endo-Surgery, Inc., Cincinnati, OH (US)

(72) Inventors: Michael J. Stokes, Cincinnati, OH (US); Edward G. Chekan, Cincinnati, OH (US); Charles J. Scheib, Loveland, OH (US); Andrew C. Yoo, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1033 days.

(21) Appl. No.: 13/804,829

(22) Filed: Mar. 14, 2013

(65) Prior Publication Data

US 2014/0263563 A1    Sep. 18, 2014

(51) Int. Cl.
  *A61B 17/08*   (2006.01)
  *A61B 17/115*  (2006.01)
  *A61B 17/00*   (2006.01)

(52) U.S. Cl.
  CPC . *A61B 17/1155* (2013.01); *A61B 2017/00557* (2013.01); *A61B 2090/0811* (2016.02)

(58) Field of Classification Search
  CPC .................. A61B 17/1155; A61B 2017/00557
  See application file for complete search history.

(56) References Cited

U.S. PATENT DOCUMENTS

| | | | |
|---|---|---|---|
| 4,805,823 A | 2/1989 | Rothfuss | |
| 5,141,516 A * | 8/1992 | Detweiler | A61B 17/11 606/153 |
| 5,205,459 A | 4/1993 | Brinkerhoff et al. | |
| 5,254,113 A * | 10/1993 | Wilk | A61B 17/1114 128/898 |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,307,541 A * | 5/1994 | Nagano | F16D 3/845 24/20 CW |
| 5,333,773 A | 8/1994 | Main et al. | |
| 5,350,104 A | 9/1994 | Main et al. | |
| 5,415,334 A | 5/1995 | Williamson, IV et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |

(Continued)

OTHER PUBLICATIONS

U.S. Appl. No. 13/688,951, filed Nov. 29, 2012.

(Continued)

*Primary Examiner* — Gregory Anderson
(74) *Attorney, Agent, or Firm* — Frost Brown Todd LLC

(57) ABSTRACT

A cuff is used to provide a form for curing fluid about the exterior of an end-to-end anastomosis site. The cuff includes a port through which fluid may be injected to reach an interior space defined between the exterior of tissue at the anastomosis site and the inner surface of the cuff. A circular stapler may be used as a mandrel for the cuff and fluid. Alternatively, inflatable balloons may be used as a mandrel. The curing fluid may comprise a mixture of fibrin and thrombin.

5 Claims, 27 Drawing Sheets

(56) References Cited

U.S. PATENT DOCUMENTS

| | | | |
|---|---|---|---|
| 5,704,534 | A | 1/1998 | Huitema et al. |
| 5,814,055 | A | 9/1998 | Knodel et al. |
| 6,978,921 | B2 | 12/2005 | Shelton, IV et al. |
| 7,000,818 | B2 | 2/2006 | Shelton, IV et al. |
| 7,143,923 | B2 | 12/2006 | Shelton, IV et al. |
| 7,303,108 | B2 | 12/2007 | Shelton, IV et al. |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,721,930 | B2 | 5/2010 | McKenna et al. |
| 7,744,624 | B2 | 6/2010 | Bettuchi |
| 7,794,475 | B2 | 9/2010 | Hess et al. |

OTHER PUBLICATIONS

U.S. Appl. No. 13/688,992, filed Nov. 29, 2012.
U.S. Appl. No. 13/693,430, filed Dec. 4, 2012.
U.S. Appl. No. 13/693,455, filed Dec. 4, 2012.
U.S. Appl. No. 13/706,827, filed Dec. 6, 2012.
U.S. Appl. No. 13/716,313, filed Dec. 17, 2012.
U.S. Appl. No. 13/716,318, filed Dec. 17, 2012.
U.S. Appl. No. 13/716,323, filed Dec. 17, 2012.

\* cited by examiner

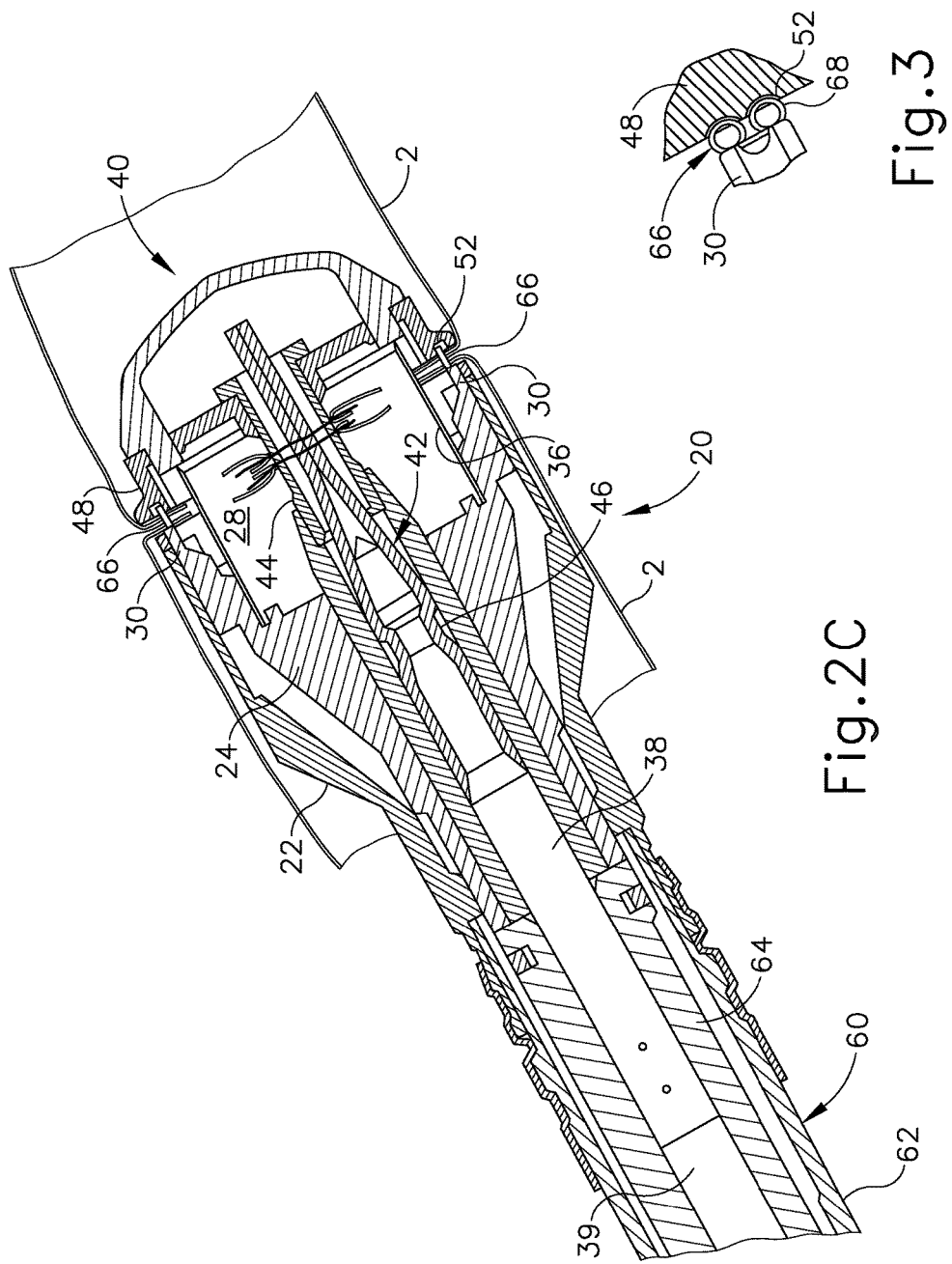

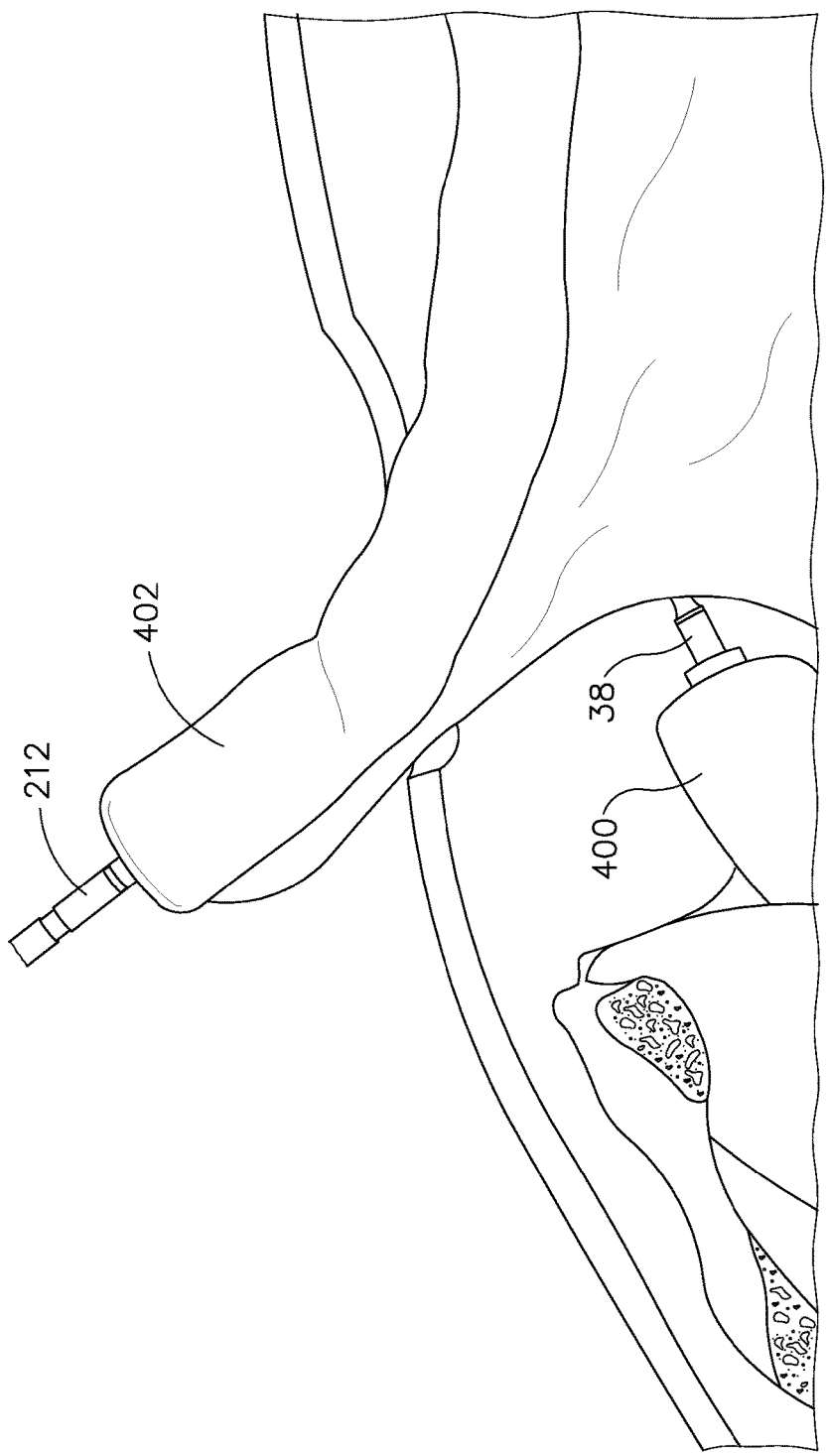

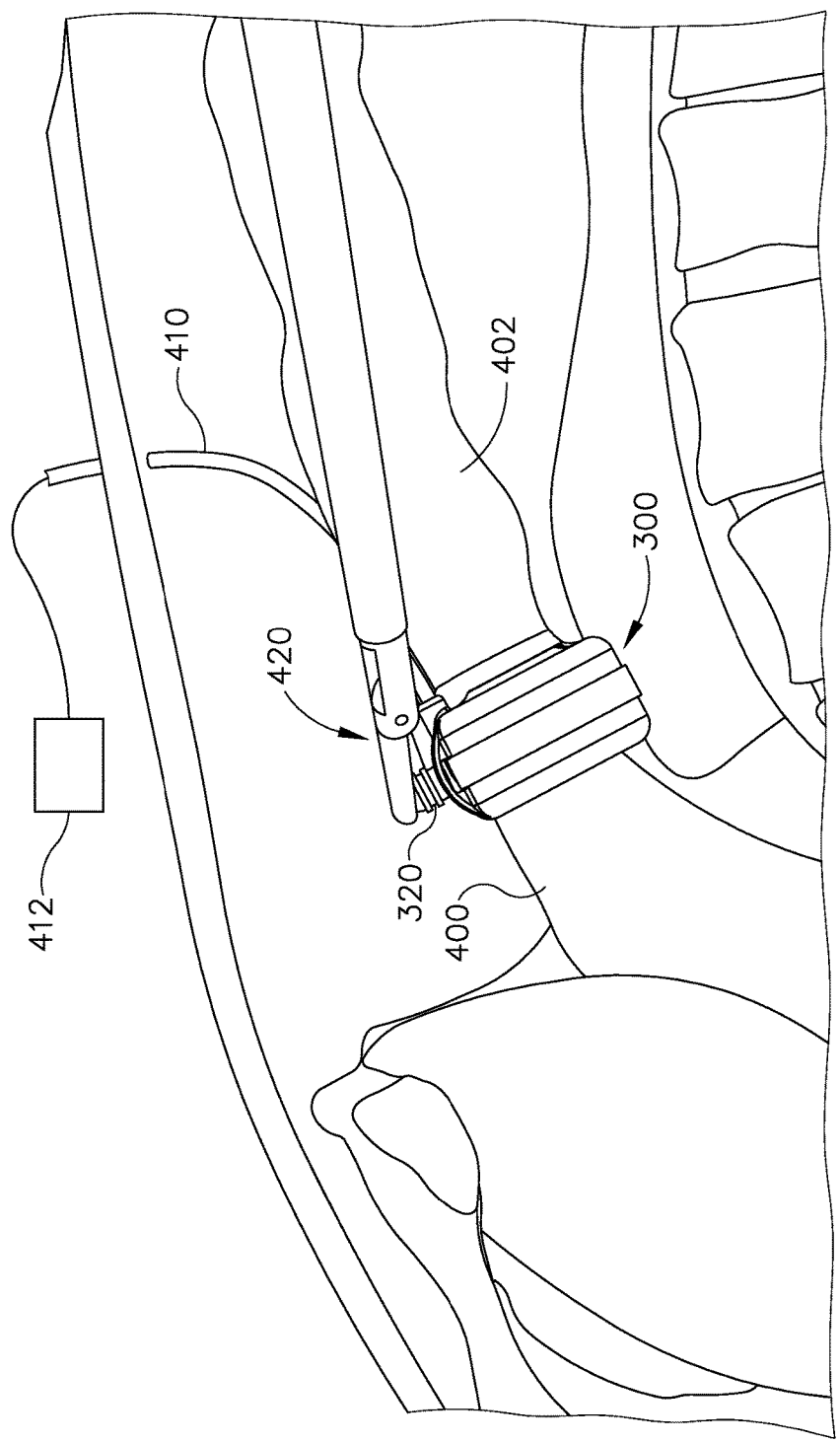

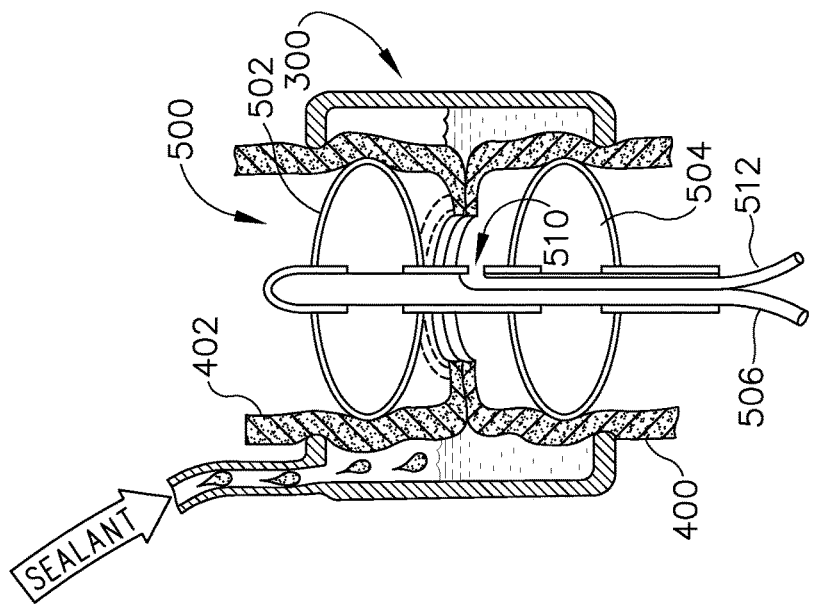
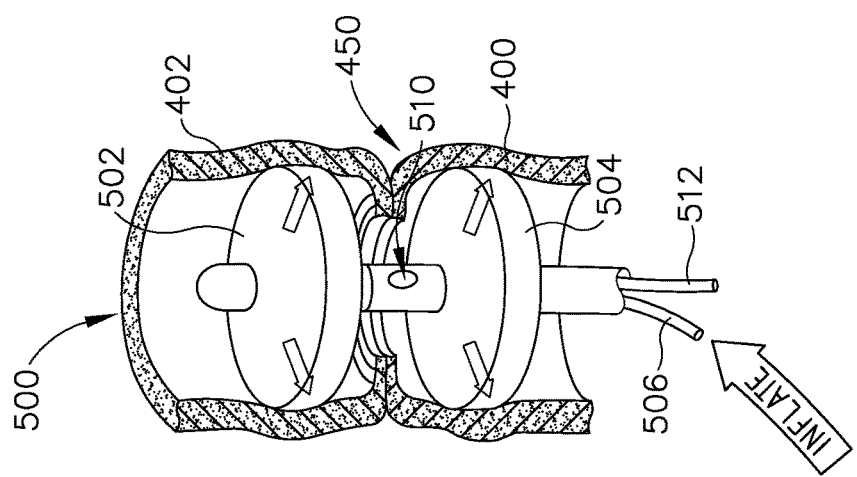
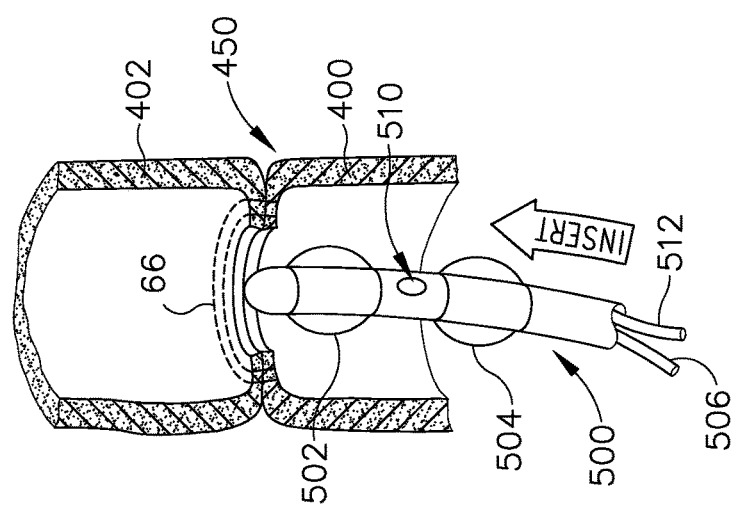

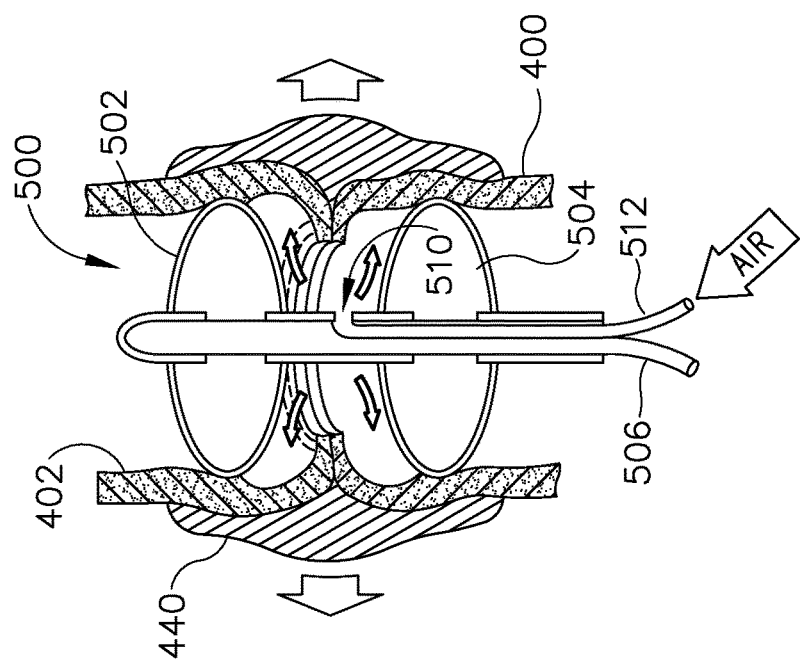
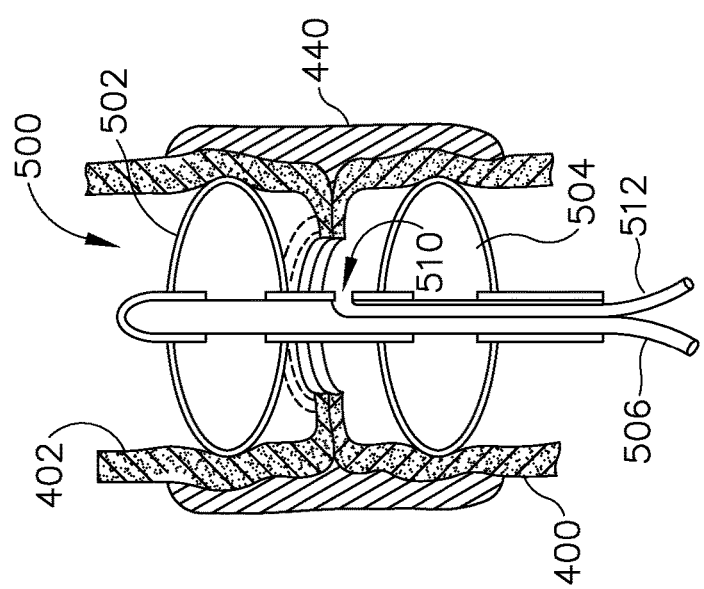

METHOD AND APPARATUS FOR SEALING END-TO-END ANASTOMOSIS

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 15A depicts a perspective view of a first stage of an exemplary procedure using the surgical instrument of FIG. 1, the anvil assembly of FIG. 7, and the cuff of FIG. 9, with the surgical instrument of FIG. 1 and the anvil assembly of FIG. 7 positioned in tissue, and with the cuff of FIG. 9 not yet introduced;

FIG. 15G depicts a perspective view of a seventh stage of the procedure of FIG. 15A;

FIG. 16A depicts a perspective view of an exemplary inflatable mandrel being positioned at an end-to-end anastomosis site, with the mandrel in a deflated state, and with the anastomosis shown in cross-section;

FIG. 16B depicts a perspective view of the mandrel of FIG. 16A positioned at the end-to-end anastomosis site, with the mandrel in an inflated state, and with the anastomosis shown in cross-section;

FIG. 16C depicts a cross-sectional view of the mandrel of FIG. 16A, with the mandrel in the inflated state, and with a sealant forming cuff receiving sealant at an exterior region of the end-to-end anastomosis;

FIG. 16D depicts a cross-sectional view of the mandrel of FIG. 16A, with the mandrel in the inflated state, and with the cuff removed to leave a formed sealant at the exterior region of the end-to-end anastomosis; and FIG. 16E depicts a cross-sectional view of the sealed anastomosis of FIG. 16D receiving pressurized fluid to test integrity of the formed sealant.

Figure 6:
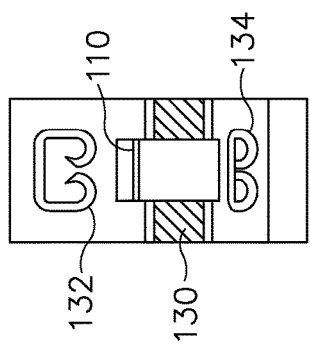
FIG. 6 depicts an diagrammatic view of the indicator window of FIG. 5 showing an exemplary indicator bar and exemplary corresponding staple representations.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 1:
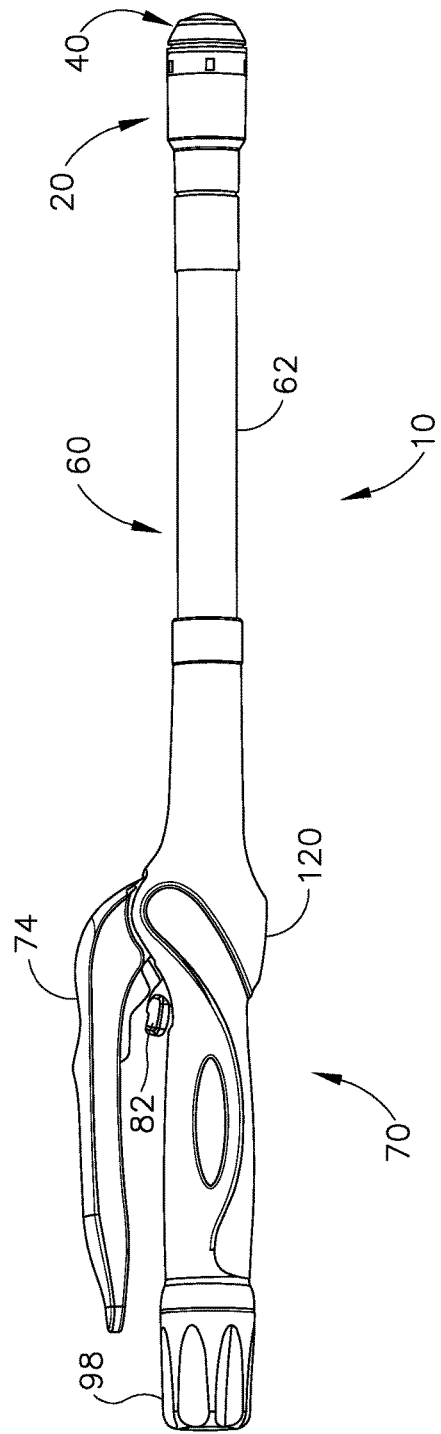
FIG. 1 depicts a side elevation view of an exemplary circular stapling surgical instrument.
Figure 2A:
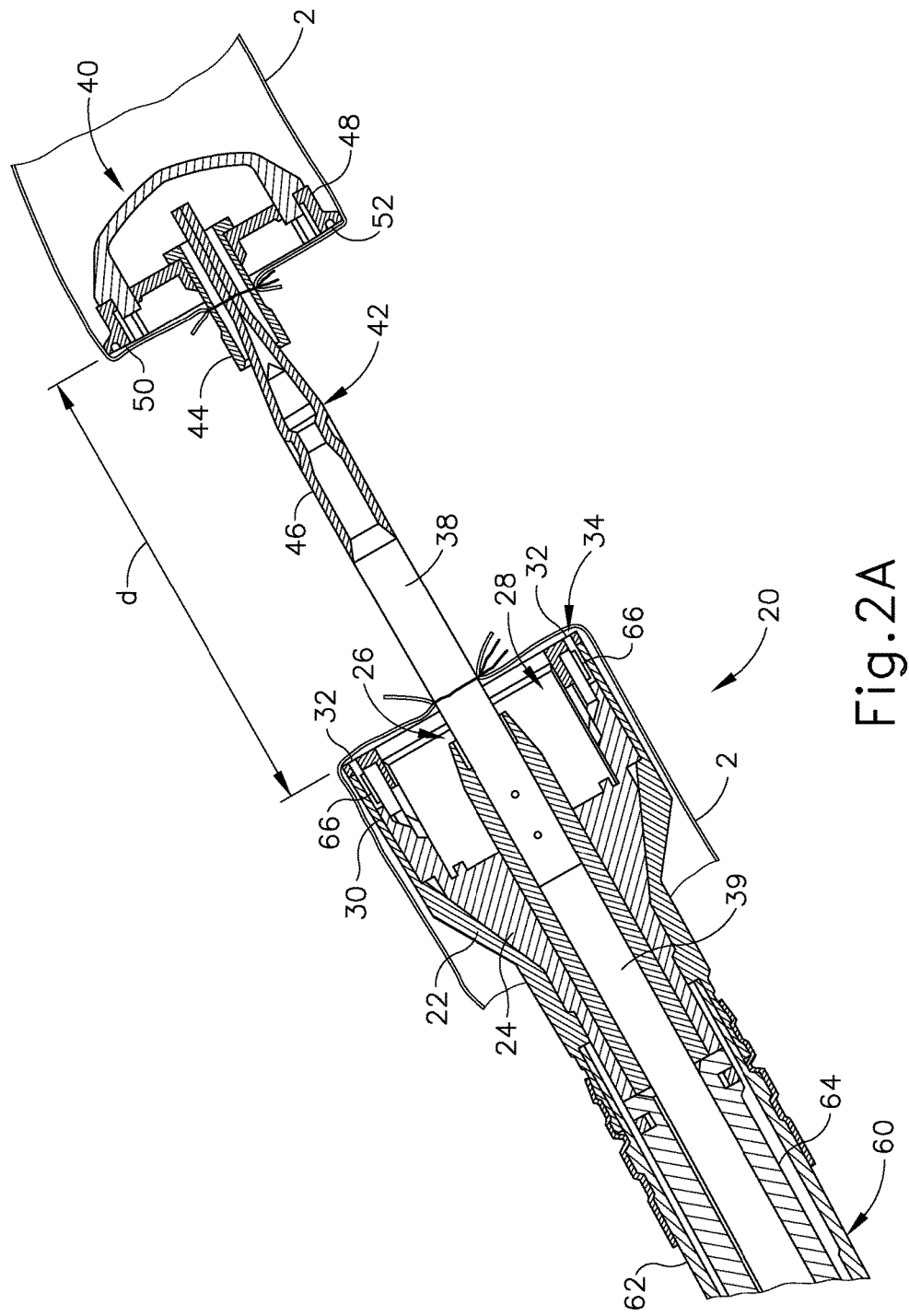
FIG. 2A depicts an enlarged longitudinal cross-section view of an exemplary stapling head assembly of the instrument of FIG. 1 showing an exemplary anvil in an open position.
Figure 2B:
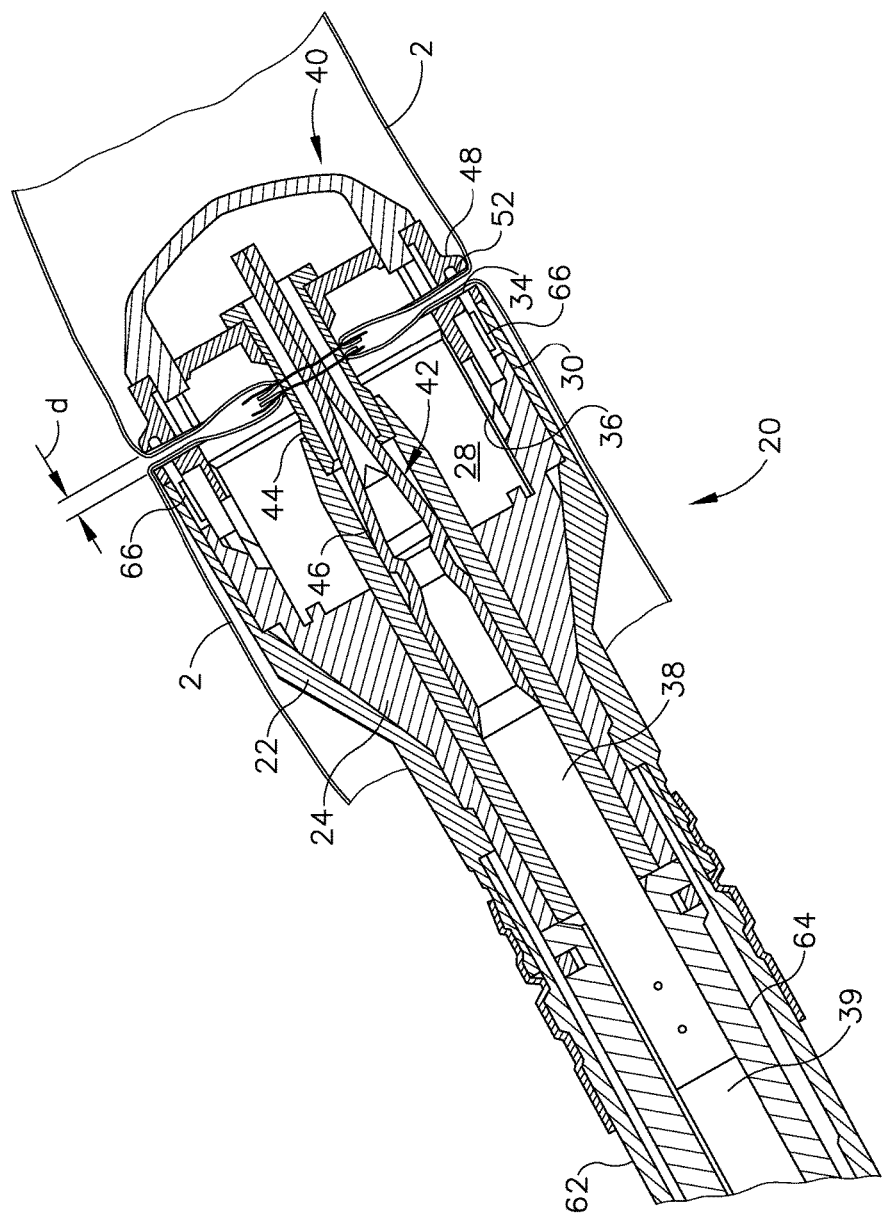
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38).

Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
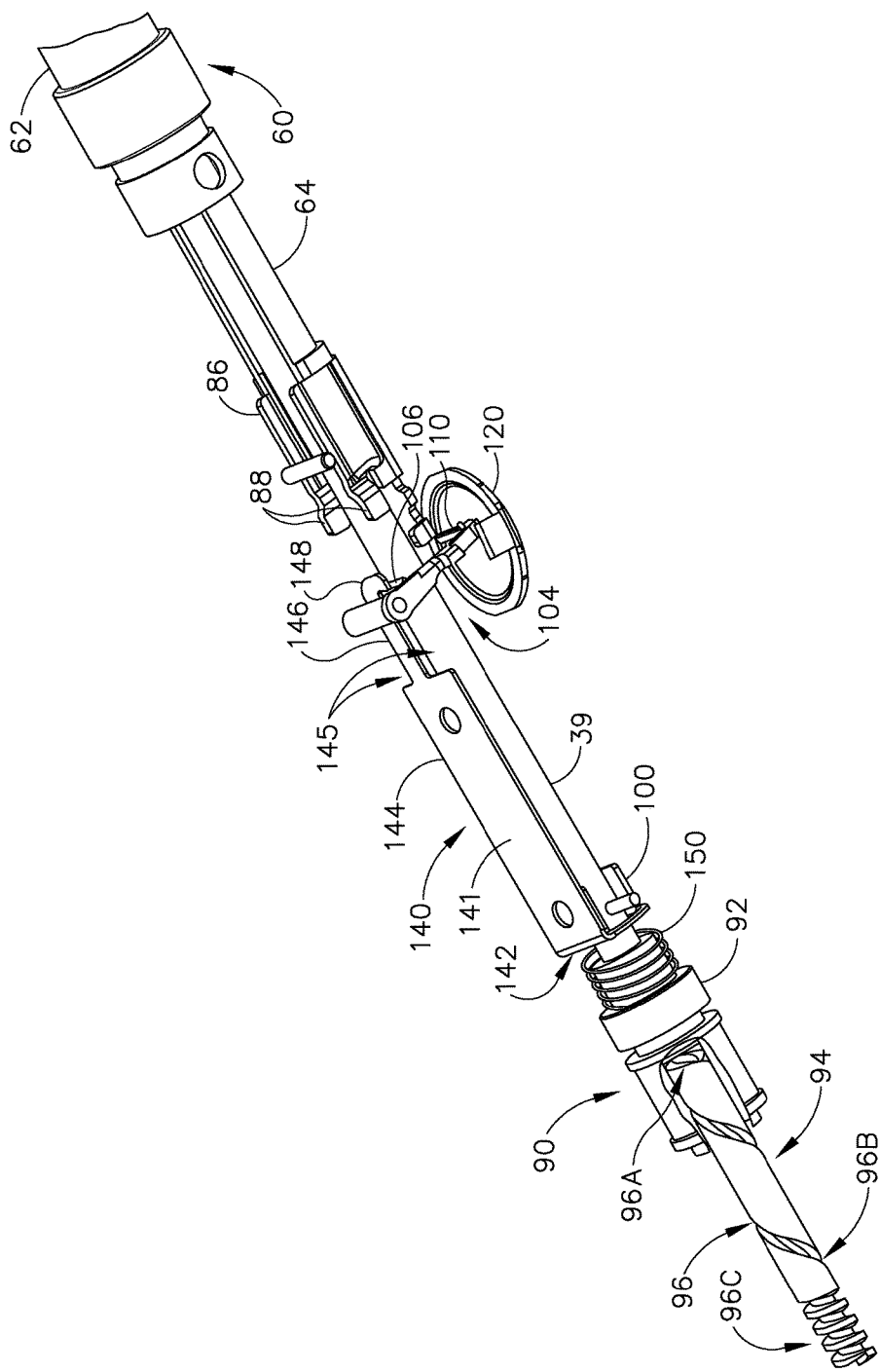
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
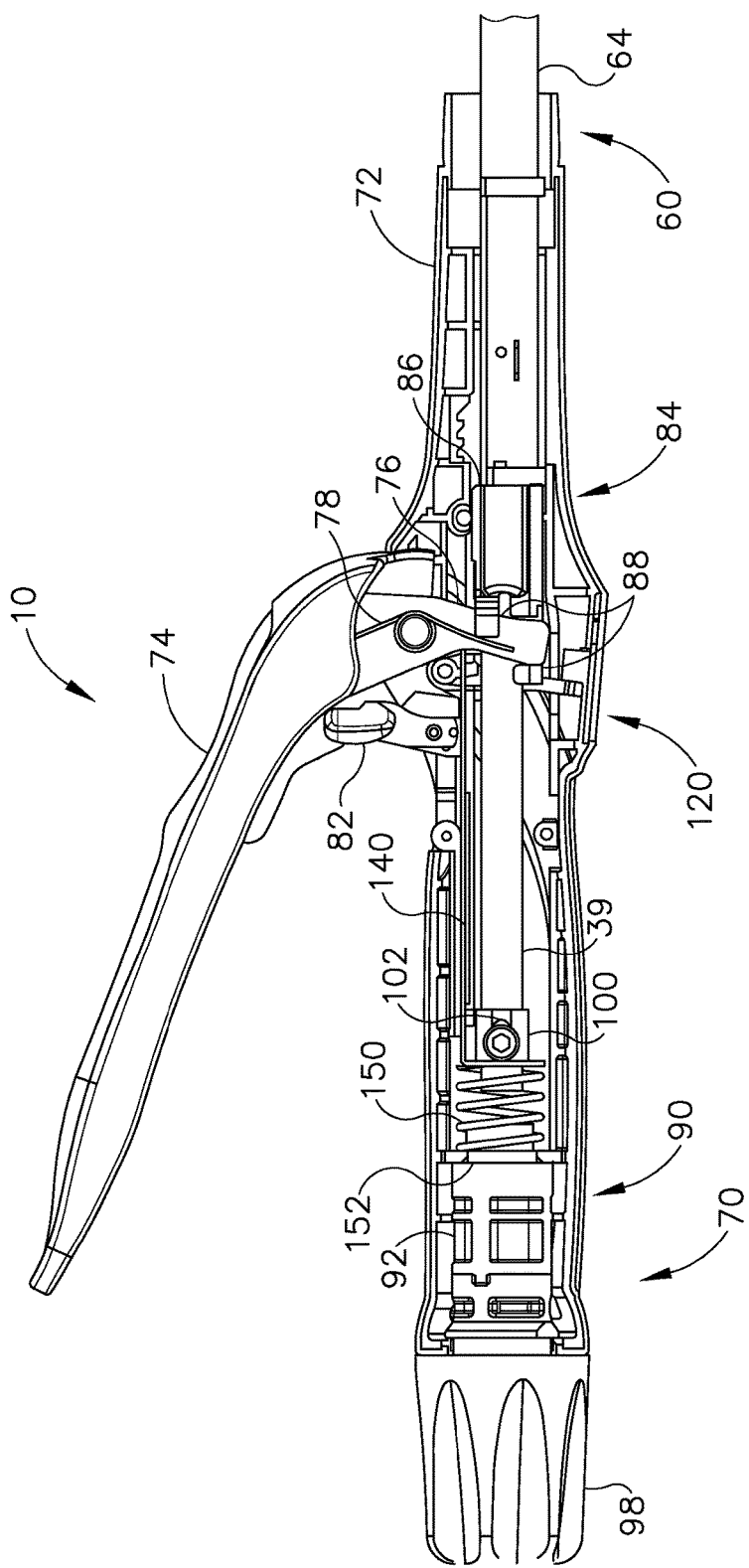
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
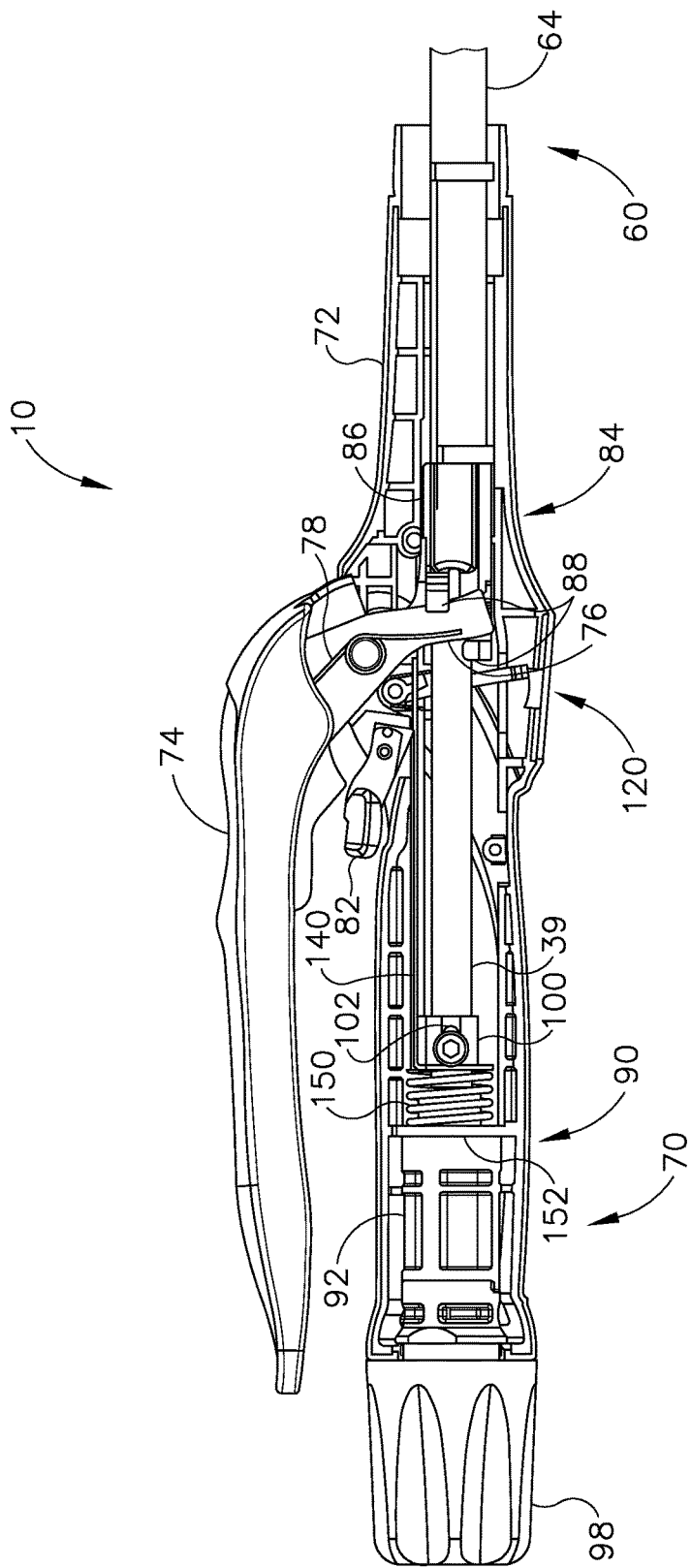
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjusting knob (98) is rotated. In some other versions, U-shaped clip (100) engages with a portion of body (72) to substantially prevent trocar actuator (39) from rotating about its axis when adjusting knob (98) is rotated. U-shaped clip (100) of the present example further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104)

shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

II. Exemplary Features for Sealing an End-to-End Anastomosis

It should be understood from the discussion above that instrument (10) may be used to form an end-to-end anastomosis. By way of example only, instrument (10) may be used to join ends of tubular anatomical structures within the gastrointestinal tract (e.g., severed intestine sections). Annular arrays of staples (66) may secure these ends together, while knife (36) may cut away excess tissue within the inner diameter of the staple (66) arrays, leaving a substantially clear path through the joined ends of the tubular anatomical structures. In some instances, the annular arrays of staples (66) may provide sufficient mechanical strength to maintain the structural integrity of the end-to-end anastomosis. This may include keeping the end-to-end anastomosis fluid tight, such that fluid does not pass out of the tubular anatomical structure at the interface of the joined ends. However there may be instances where the anastomosis is not sufficiently fluid tight due to factors involving the patient (e.g., physiology, inappropriate subsequent activity, etc.) and/or the operating surgeon (e.g., operator error). It may therefore be desirable to provide additional securing and sealing of an end-to-end anastomosis to supplement the securing and sealing provided by staples (66). The discussion below relates to various merely illustrative examples of how an end-to-end anastomosis may be supplemented. Other examples will be apparent to those of ordinary skill in the art in view of the teachings herein.

Figure 7:
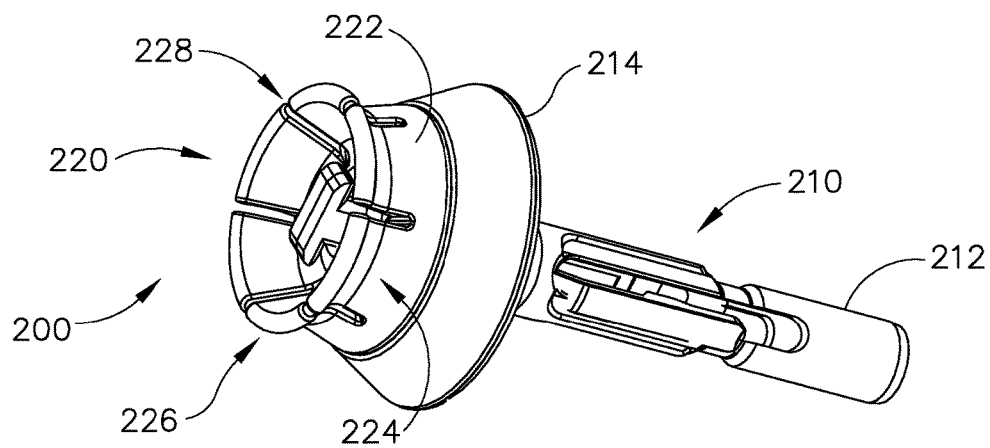
FIG. 7 depicts a perspective view of an exemplary alternative anvil assembly that may be used with the surgical instrument of FIG. 1.
Figure 8:
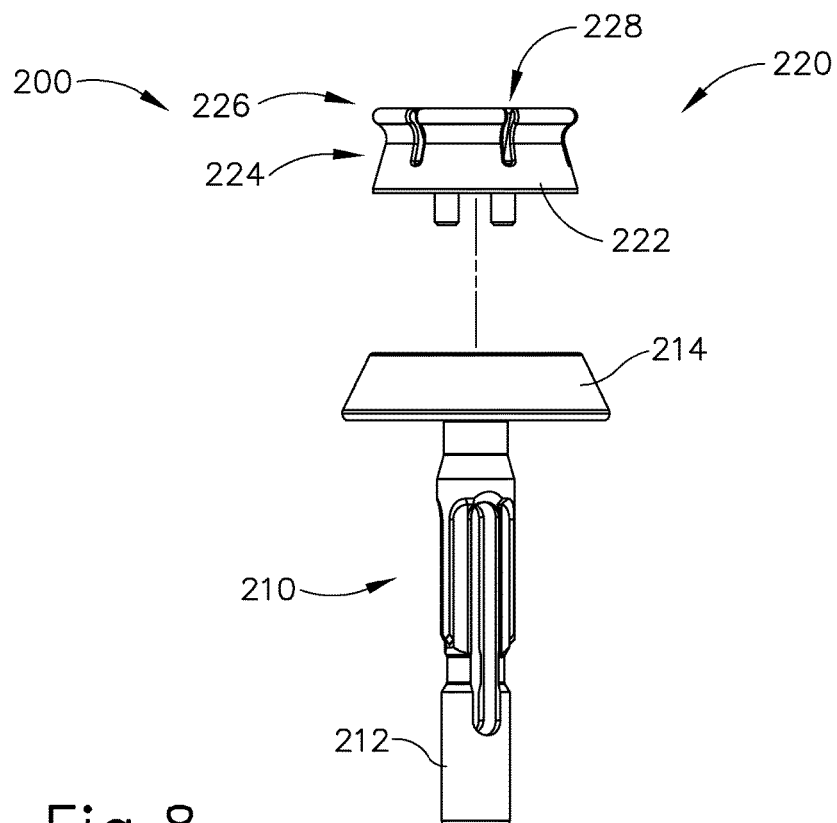
FIG. 8 depicts an exploded elevational view of the anvil assembly of FIG. 7.
Figure 9:
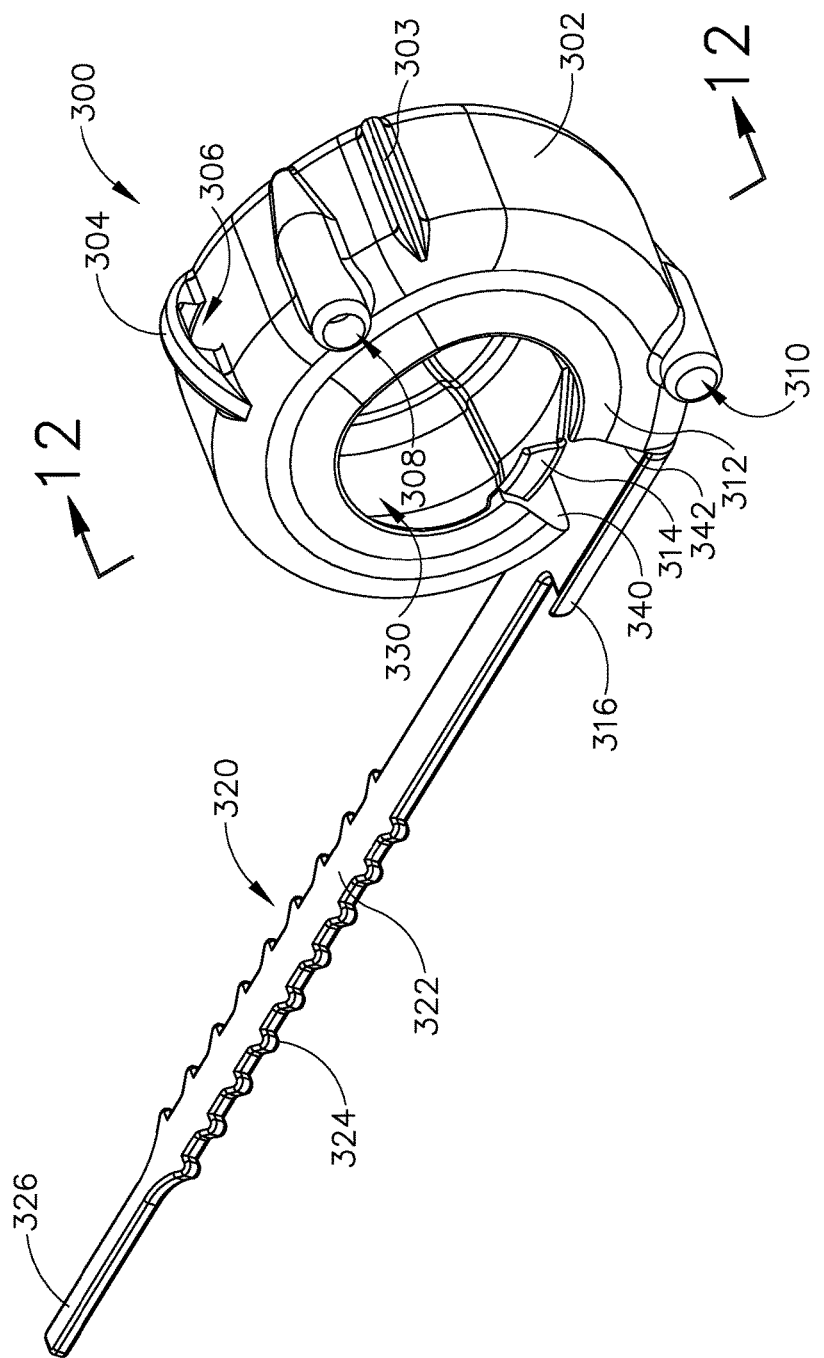
FIG. 9 depicts an exemplary sealant forming cuff that may be used with the surgical instrument of FIG. 1 and the anvil assembly of FIG. 7.
Figure 10:
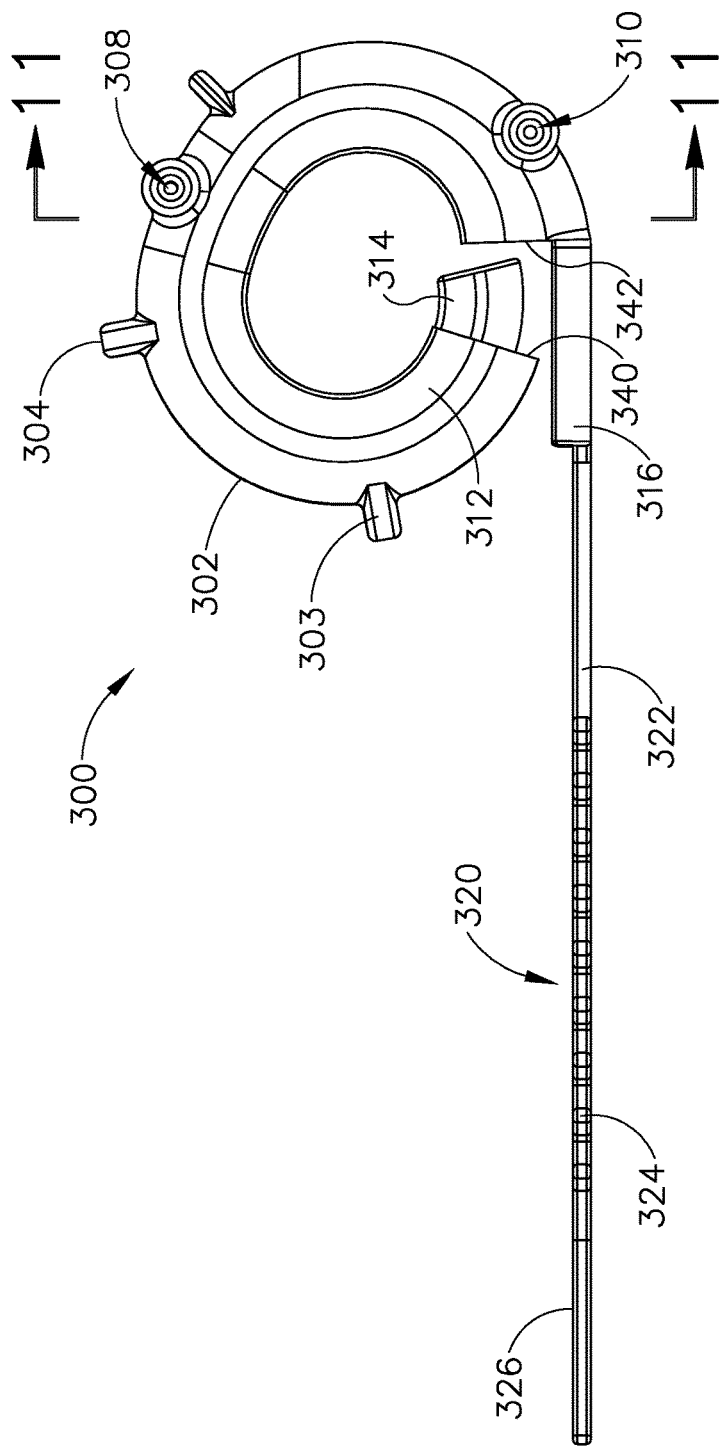
FIG. 10 depicts a side elevational view of the cuff of FIG. 9.
Figure 11:
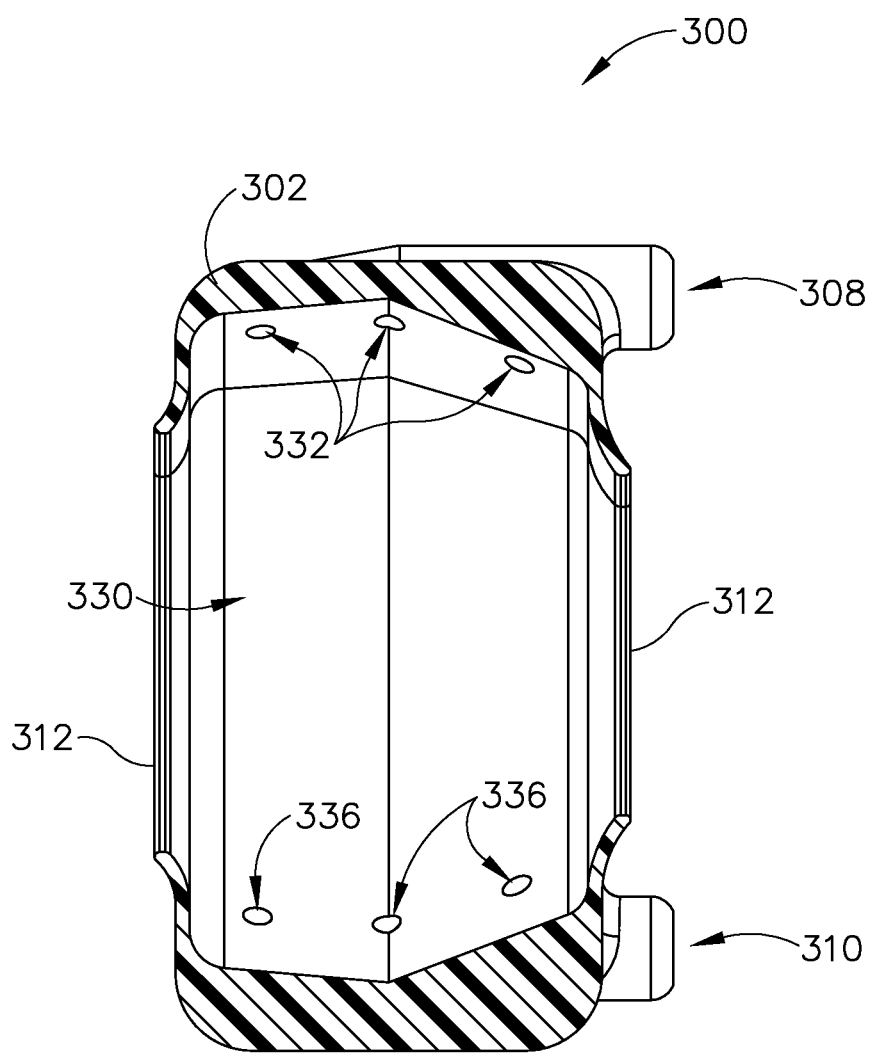
FIG. 11 depicts a cross-sectional view of the cuff of FIG. 9, taken along line 11-11 of FIG. 10.

FIG. 7 shows an exemplary alternative anvil assembly (200) that may be used with instrument (10) described above. Anvil assembly (200) comprises an anvil (210) and a mandrel head (220). Anvil (210) is substantially identical to anvil (40) described above. Anvil (210) includes a proximal shaft (212) that is configured to selectively couple with trocar (38) just like proximal shaft (42) of anvil (40). Anvil (210) also includes an anvil head (214) that is similar to anvil head (48) described above. Mandrel head (220) is secured to the top of anvil head (214). Mandrel head (220) includes a body (222) defining an inwardly recessed portion (224) and an outwardly flared portion (226) above inwardly recessed portion (224). A series of slots (228) are defined in body (222). Slots (228) are configured to allow body (222) to deform slightly when forces are exerted radially inwardly on recessed portion (224) and/or flared portion (226). By way of example only, body (222) may comprise an elastic material.

Figure 12:
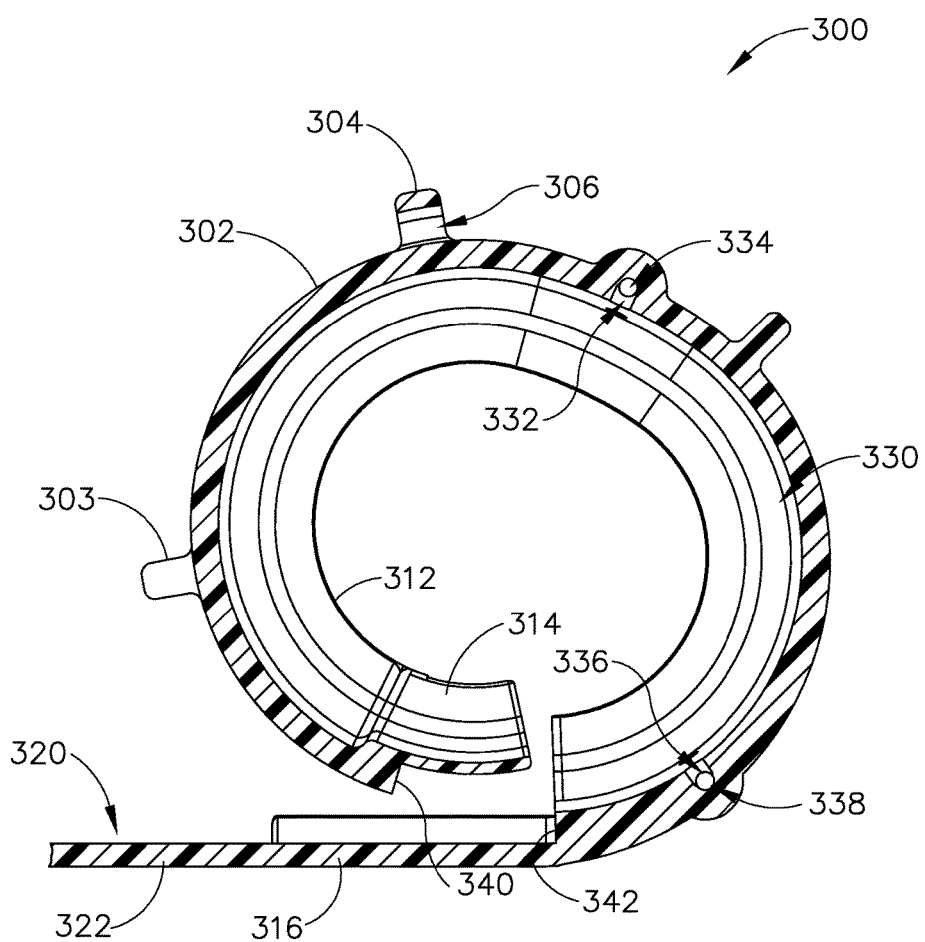
FIG. 12 depicts a cross-sectional view of the cuff of FIG. 9, taken along line 12-12 of FIG. 9.
Figure 13:
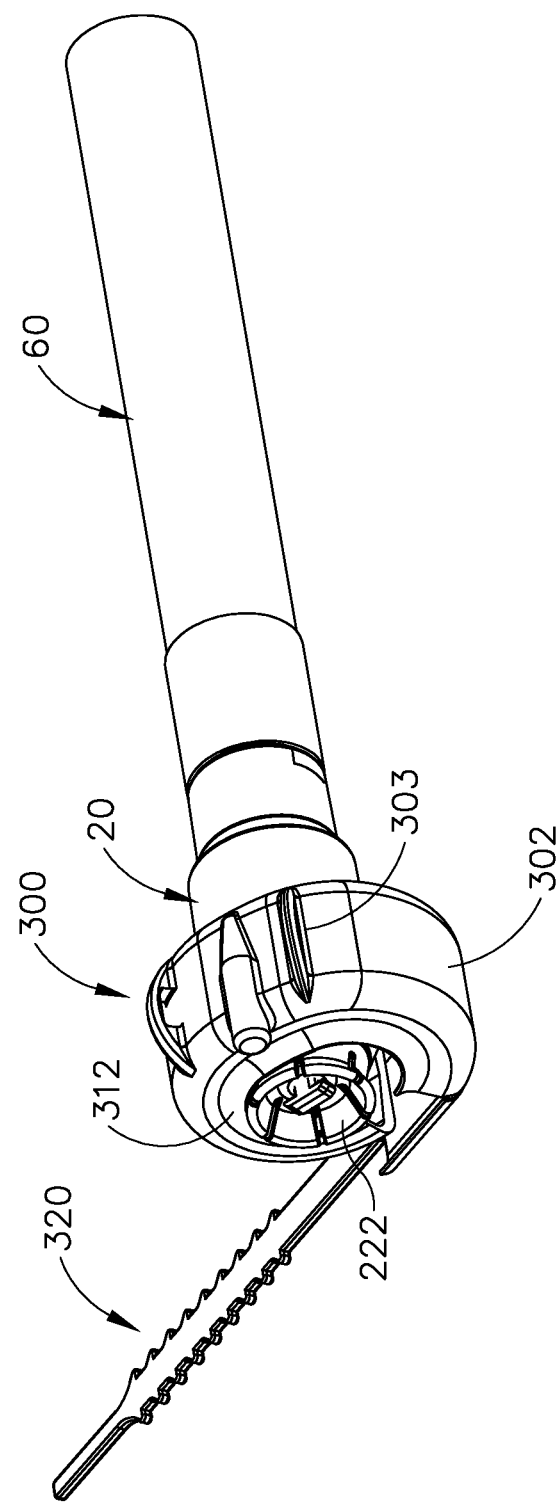
FIG. 13 depicts a perspective view of the cuff of FIG. 9 positioned about a distal portion of the surgical instrument of FIG. 1 and the anvil assembly of FIG. 7.

FIGS. 9-12 show an exemplary sealant forming cuff (300) that may be used with instrument (10) and anvil assembly (200). Cuff (300) of this example comprises a body (302) with a pair of ports (308, 310) and a fastening strap (320). Body (302) is formed of silicone in the present example, though it should be understood that any other suitable material(s) may be used to form body (302) (e.g., polyethylene, PET, polypropylene, PTFE, biocompatible metal, etc.). Body (302) includes two ribs (303) for grasping/manipulation and a strap receiving rib (304). Strap receiving rib (304) defines an opening (306) that is configured to receive strap (320). Ports (308, 310) of the present example are in fluid communication with the interior (330) of cuff (300). In particular, and as best seen in FIG. 12, port (308) is in fluid communication with a conduit (334) formed in body (302) while port (310) is in fluid communication with a conduit (338) formed in body (302). As best seen in FIGS. 12-13 together, conduit (334) is in fluid communication with a series of openings (332) while conduit (338) is in fluid communication with openings (336). Thus, port (308) is in fluid communication with the interior (330) of cuff (300) via conduit (334) and openings (332); while port (310) is in fluid communication with the interior (330) of cuff (300) via conduit (338) and openings (336). Ports (308, 310) are configured to couple with external fluid sources, such as one or more syringes that are operable to drive fluid into ports (308, 310). Various suitable kinds of fluid sources that may be coupled with ports (308, 310), as well as various suitable ways in which such fluid sources may be coupled with ports (308, 310), will be apparent to those of ordinary skill in the art in view of the teachings herein. Similarly, various kinds of fluids that may be communicated through ports (308, 310) will be described in greater detail below, while still other kinds of fluids that may be communicated through ports (308, 310) will be apparent to those of ordinary skill in the art in view of the teachings herein.

Cuff (300) is configured to transition between an open position and a closed position. When cuff (300) is in the closed position, a first seam face (340) presented by body (302) is apposed with a second seam face (342) presented by body (302), such that a seam exists at this apposition site. In the closed position, cuff (300) closes around tissue encompassing stapling head assembly (20) and anvil assembly (200) as will be described in greater detail below. When cuff (300) is in a fully closed position around tissue, one lip (312) of cuff (300) seals against tissue disposed over stapling head assembly (20) while another lip (312) of cuff (300) seals against tissue disposed over anvil assembly (200). Lips (312) are positioned along generally radially extending planes. To assist with this seal at the seam of cuff (300), body (302) includes an inner tongue (314) and an outer tongue (316). Tongue (314) extends within the interior (330) of cuff (300) when cuff (300) is in the closed position, further closing off an inner portion of the seam defined by apposed seam faces (340, 342). Tongue (316) extends along part of the exterior of cuff (300) when cuff (300) is in the closed position, further closing off an outer portion of the seam defined by apposed seam faces (340, 342).

To hold cuff (300) in the closed position, strap (320) may be passed through opening (306) of strap receiving rib (304). Strap (320) comprises an elongate strap body (322) that extends from tongue (316). Strap body (322) defines a plurality of barbs (324) and a grasping region (326) distal to barbs (324). To secure strap (320), the operator may grasp grasping region (326) and pass grasping region (326) through opening (306). The operator may then continue to pull grasping region (326) to pull barbs (324) through opening (306). Barbs (324) may effectively ratchet through opening (306) as the operator continues to pull strap (320) until strap (320) is sufficiently tight. The operator may then release strap (320). The configuration of barbs (324) may prevent strap (320) from being pulled back through opening (306) in the opposite direction. Thus, barbs (324) and strap receiving rib (304) may cooperate to maintain tension in strap (320), thereby holding cuff (300) in a closed position.

Figure 14:
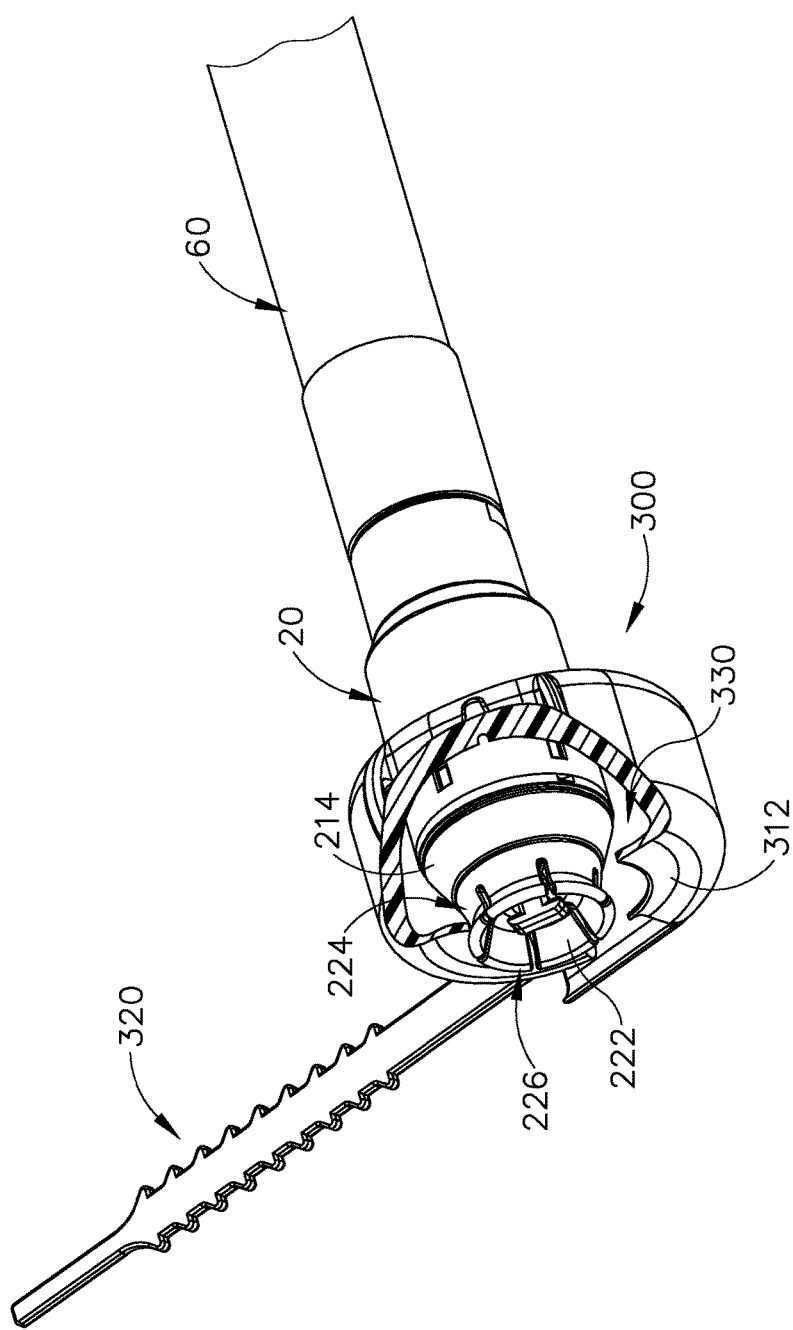
FIG. 14 depicts an enlarged perspective view of the cuff of FIG. 9 positioned about a distal portion of the surgical instrument of FIG. 1 and the anvil assembly of FIG. 7, with a portion of the cuff cut away.

FIGS. 13-14 show cuff (300) positioned in relation to a stapling head assembly (20) and an anvil assembly (200). As shown, one lip (312) is positioned within recessed portion (224) of mandrel head (220). The other lip (312) is positioned about stapling head assembly.

Figure 15B:
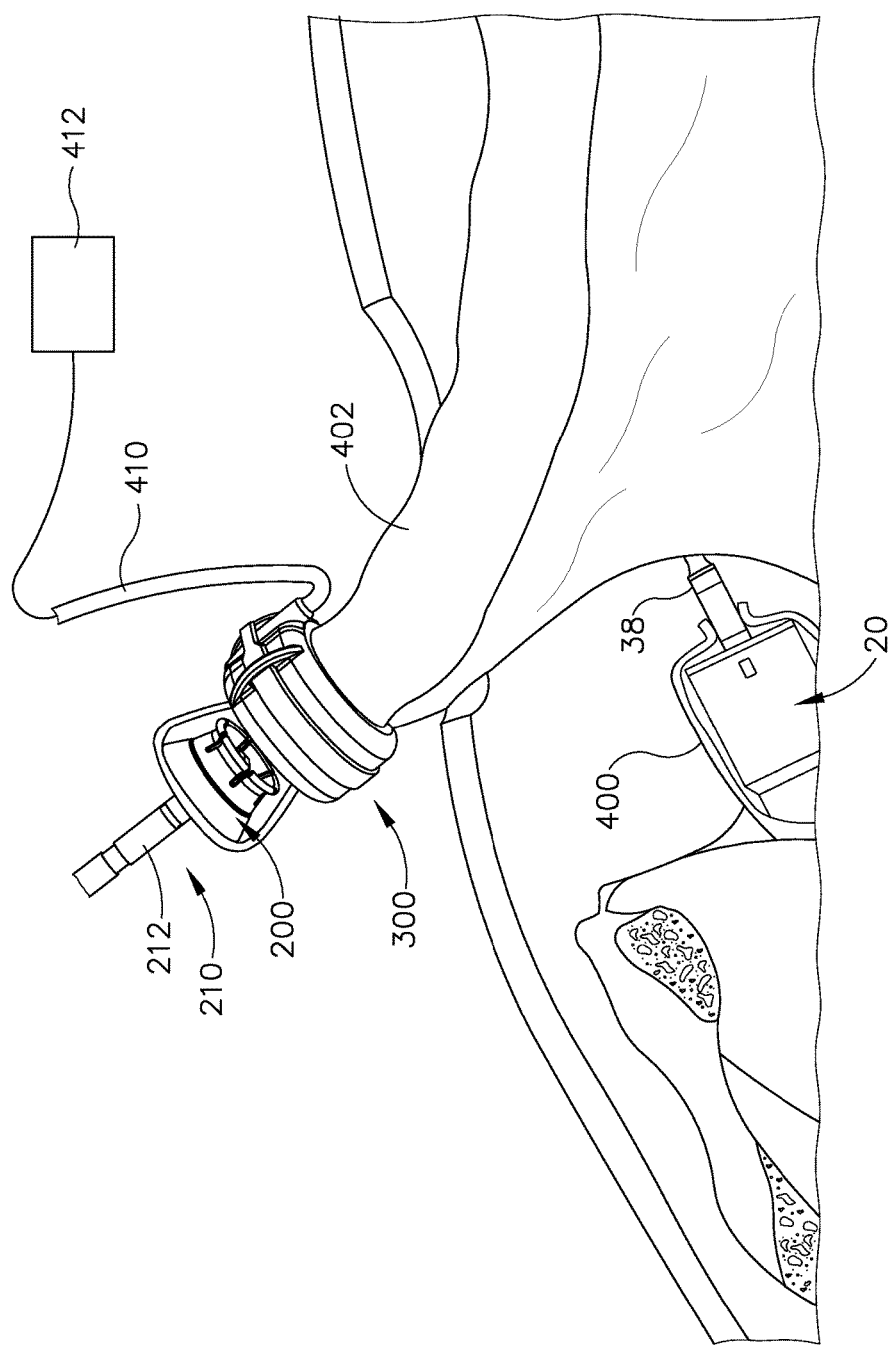
FIG. 15B depicts a perspective view of a second stage of the procedure of FIG. 15A, with portions of an intestine shown in cross-section to reveal a portion of the surgical instrument of FIG. 1 and a portion of the anvil assembly of FIG. 7.

FIGS. 15A-15K show instrument (10), anvil assembly (200), and cuff (300) being used in a procedure to join the end of one intestine section (400) to the end of another severed intestine section (402). While the present example is being carried out in the context of the intestines, it should be understood that instrument (10), anvil assembly (200), and cuff (300) may instead be used in other locations within the gastrointestinal tract or elsewhere within a patient. As shown in FIG. 15A, instrument (10) has been positioned such that trocar (38) protrudes from the end of one intestine section (400). A suture (not shown), linear stapler, or other device has been used to form a purse-string arrangement to generally secure the severed end of intestine section (400) around trocar (38). Anvil assembly (200) has been positioned such that shaft (212) protrudes from the end of the other intestine section (402). A suture (not shown), linear stapler, or other device has been used to form a purse-string arrangement to generally secure the severed end of intestine section (402) around shaft (212).

Figure 15C:
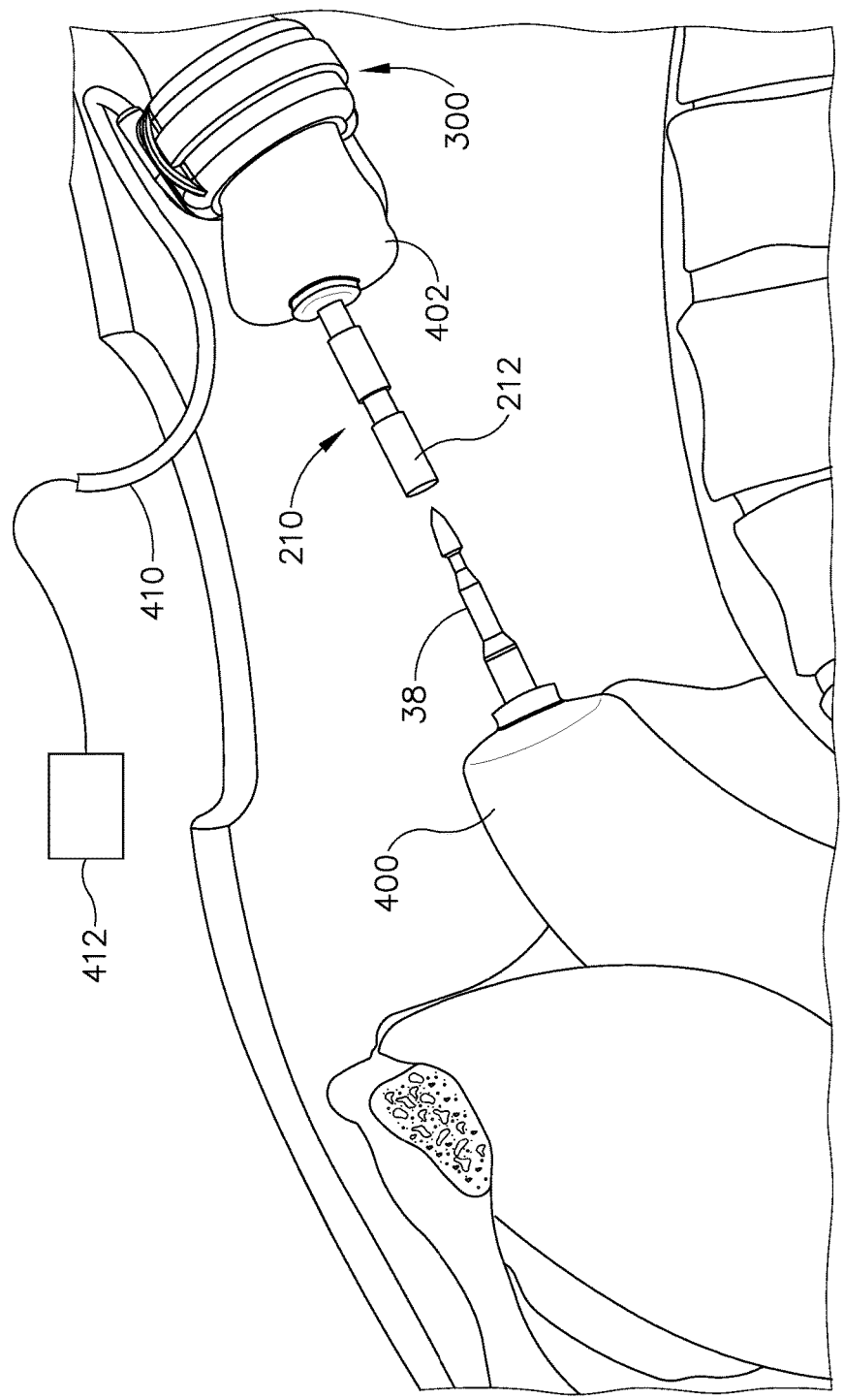
FIG. 15C depicts a perspective view of a third stage of the procedure of FIG. 15A.
Figure 15D:
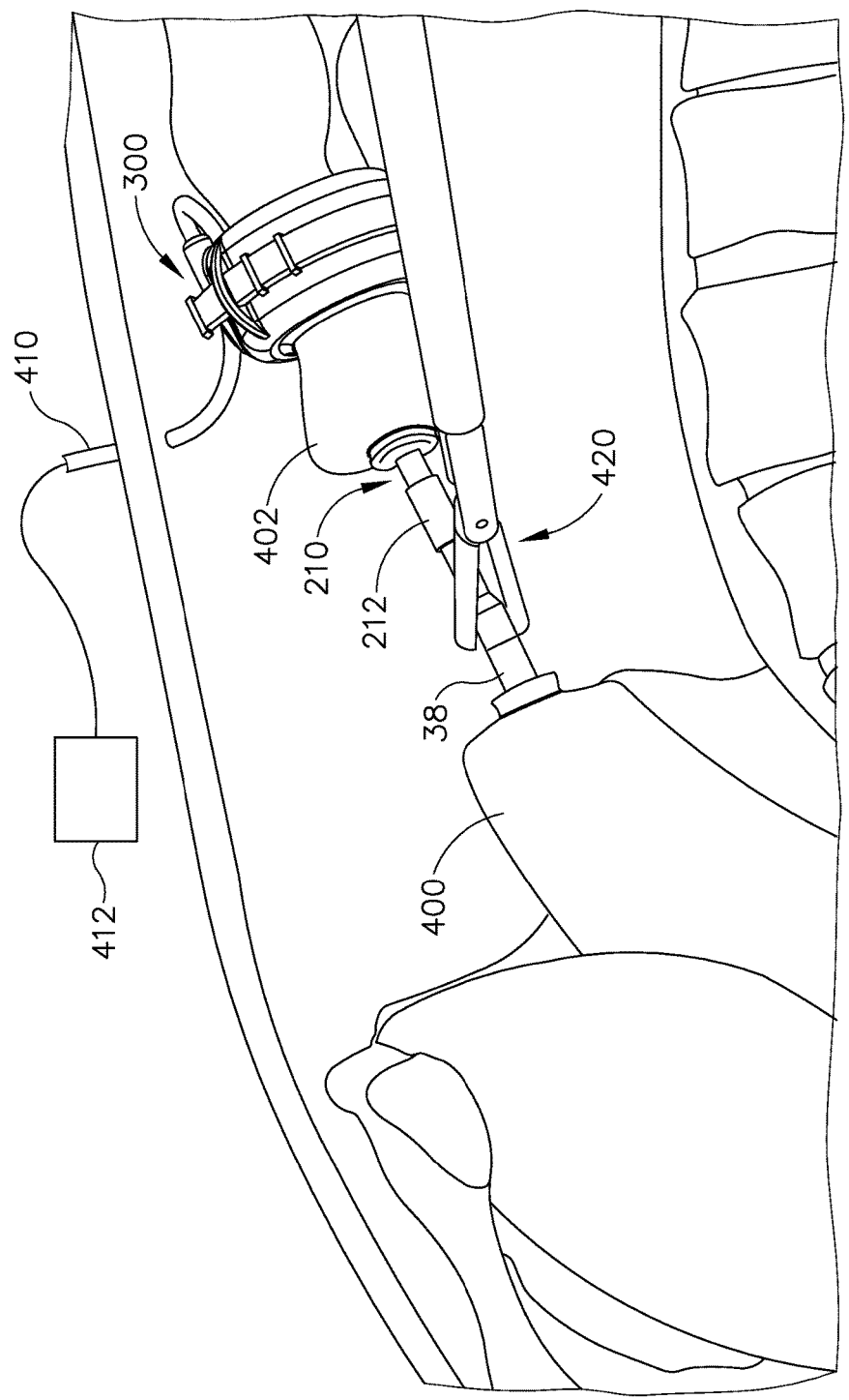
FIG. 15D depicts a perspective view of a fourth stage of the procedure of FIG. 15A.

With instrument (10) and anvil assembly (200) positioned, cuff (300) is placed around intestine section (402) as shown in FIG. 15B. As shown, a conduit (410) is coupled with port (308) and extends to a fluid source (412). While not shown, it should be understood that a similar conduit may be coupled with port (310). This additional conduit may be further coupled with the same fluid source (412) or some other fluid source. Next, the operator grasps shaft (212) and maneuvers to align shaft (212) with trocar (38) as shown in FIG. 15C. This alignment may also require manipulation of instrument (10) to properly orient trocar (38). The operator then slides shaft (212) onto trocar (38), thereby coupling shaft (212) with trocar (38) as shown in FIG. 15D and as described above. The operator then rotates knob (98) to retract trocar (38), thereby pulling anvil assembly (200) toward stapling head assembly (20). This clamps tissue of intestine sections (400, 402) between anvil assembly (200) and stapling head assembly (20) as shown in FIG. 15E.

Figure 15E:
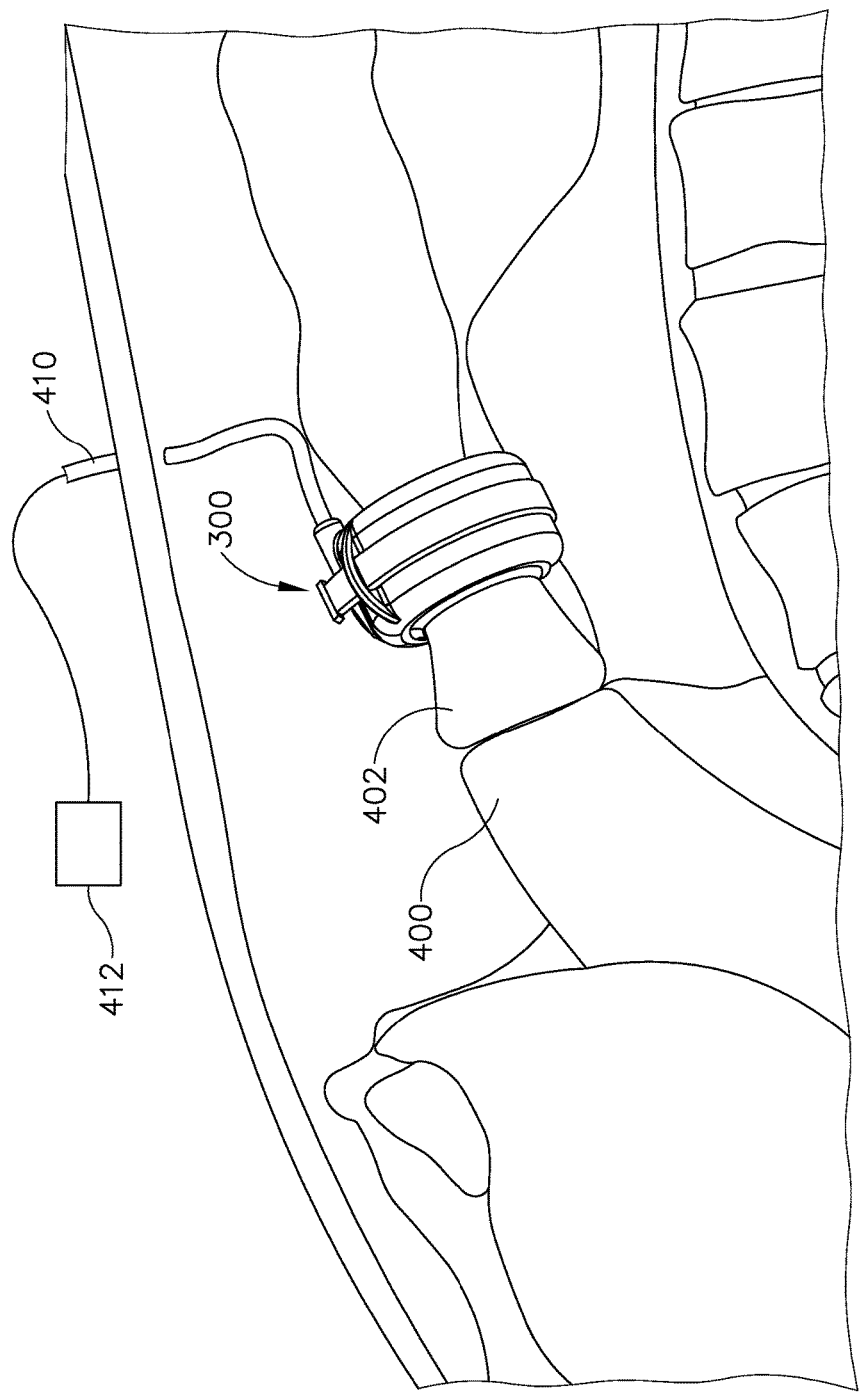
FIG. 15E depicts a perspective view of a fifth stage of the procedure of FIG. 15A.
Figure 15F:
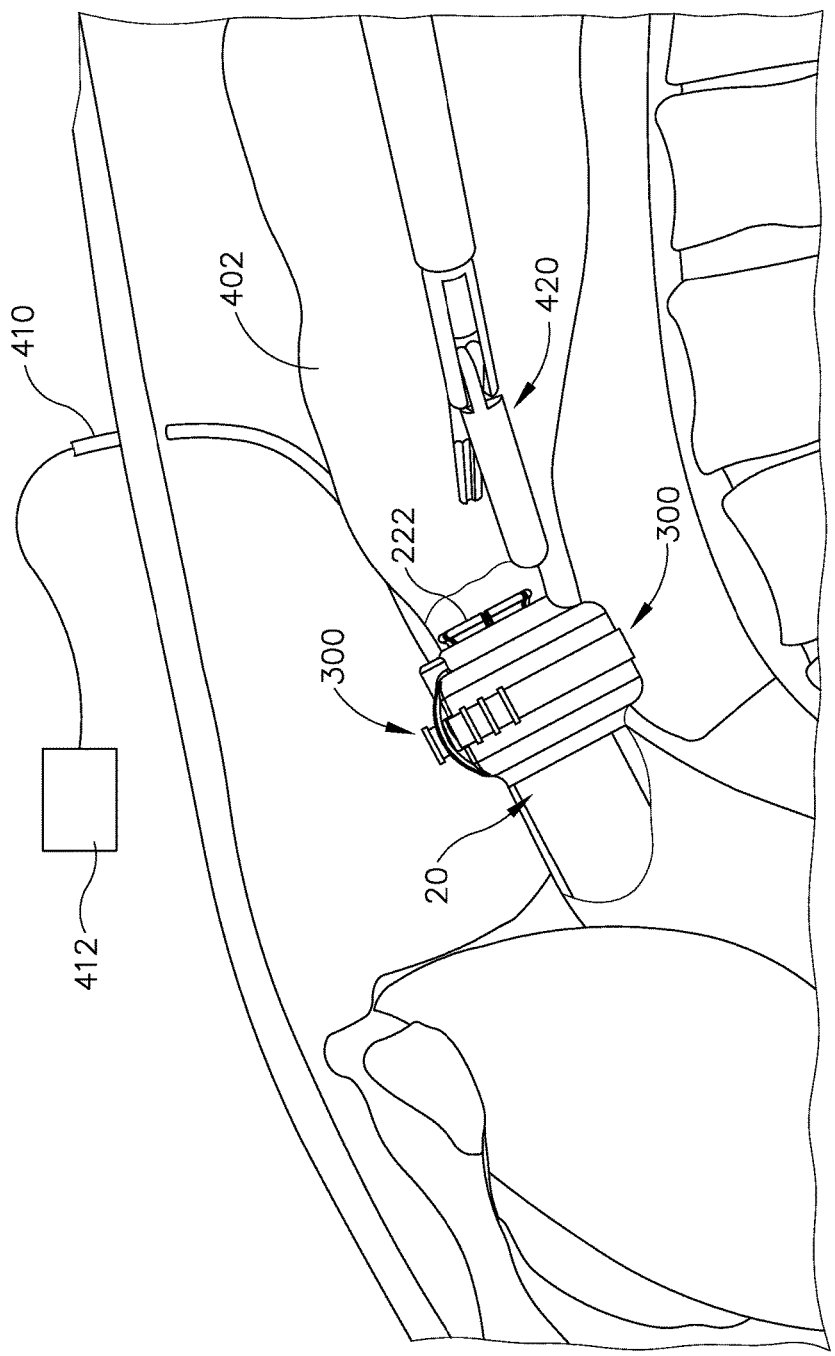
FIG. 15F depicts a perspective view of a sixth stage of the procedure of FIG. 15A.

Once the ends of intestine sections (400, 402) have been clamped together as shown in FIG. 15E, cuff (300) is then slid into position about the joined intestine sections (400, 402) as shown in FIG. 15F. By way of example only, cuff (300) may be slid into position by grasping rib (303). With cuff (300) in position, one lip (312) is positioned at a region corresponding to recessed portion (224) of mandrel head (220); while the other lip (312) is positioned at a region corresponding to stapling head assembly (20). Thus, mandrel head (220) and stapling head assembly (20) provide structural support to tissue engaged by cuff (300) when cuff (300) is closed. Strap (320) is then pulled through opening (306) to secure cuff (300) in position as shown in FIG. 15G. It should be understood that conventional graspers (420) may be used to position cuff (300) and manipulate strap (320). It should also be understood that, in some instances, strap (320) may be partially pulled through opening (306) before cuff (300) reaches the position shown in FIG. 15F. For instance, while cuff (300) is in the position shown in FIG. 15B, 15C, 15D, or 15E, the operator may start strap (320) through opening (306) but not tighten strap (320), such that cuff (300) may still slide substantially freely along intestine section (402). In either case, when cuff (300) is secured by strap (320) as shown in FIG. 15G, lips (312) provide a fluid tight seal against the adjacent tissue of intestine sections (400, 402). Tongues (314, 316) provide a fluid tight seal at the seam defined by the interface of apposed seam surfaces (340, 342).

Figure 15H:
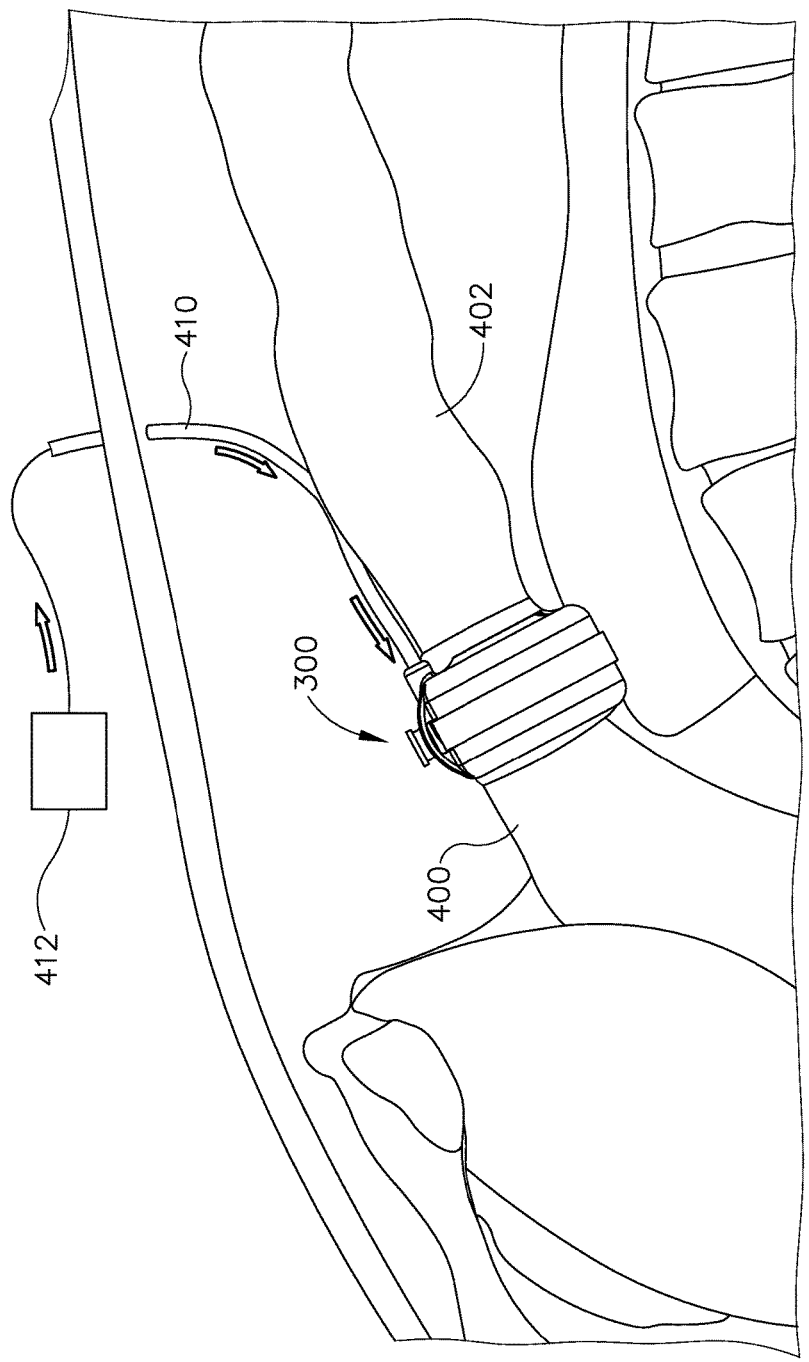
FIG. 15H depicts a perspective view of a eighth stage of the procedure of FIG. 15A.

Once cuff (300) is secured firmly in place, instrument (10) may be actuated to drive staples (66) through the tissue at the clamped ends of intestine sections (400, 402) and to drive knife (36) to cut away excess tissue within the inner diameter of the staple (66) arrays. Before or after instrument (10) is actuated, fluid source (412) may be actuated to drive fluid into the interior (330) of cuff (300) via conduit (410) and port (308), as shown in FIG. 15H. As noted above, port (310) may also receive fluid, either from the same fluid source (412) or from a different fluid source. It should be understood that ports (308, 310) may receive fluid simultaneously, in succession, or in any other suitable fashion.

The fluid or combination of fluids delivered to the interior (330) of cuff (300) is/are selected such that it/they will cure to form a sealing body around the exterior of the anastomosis of joined intestine sections (400, 402). By way of example only, a combination of fibrin and thrombin may be delivered to the interior (330) of cuff (300). In some instances, fibrinogen and thrombin are combined, and this combination is communicated through conduit (410) to port (308). In some other instances, fibrin is communicated through one conduit (410) to port (308) while thrombin is communicated through another conduit to port (310), such that the fibrin and thrombin first mix together within the interior (330) of cuff (300). As additional merely illustrative examples, fluids such as lysine derived urethane or resorbable hydrogel (human derived or synthetic) may be communicated to ports (308, 310). Other suitable fluids that may be used will be apparent to those of ordinary skill in the art in view of the teachings herein.

Figure 15I:
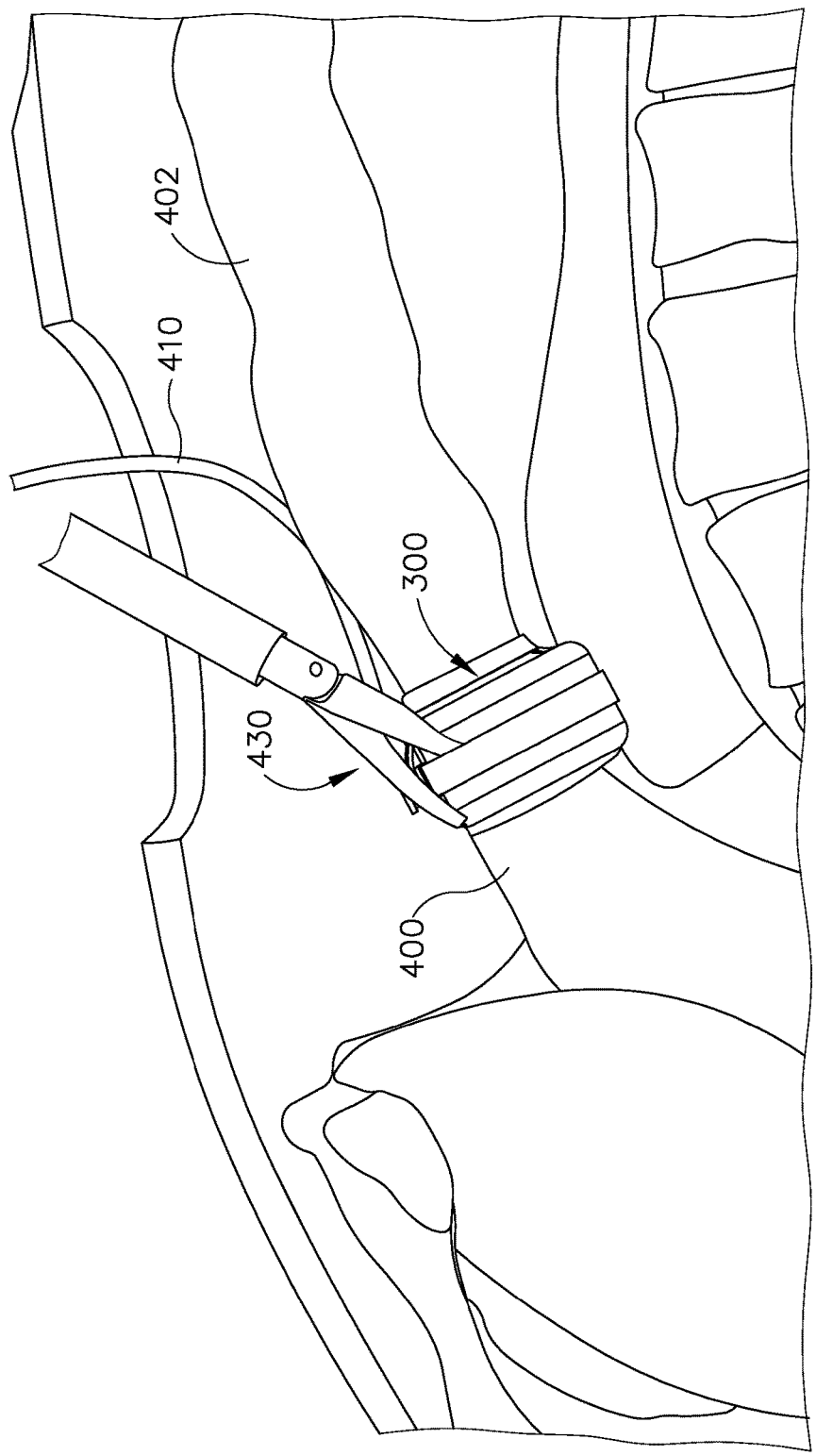
FIG. 15I depicts a perspective view of a ninth stage of the procedure of FIG. 15A.
Figure 15J:
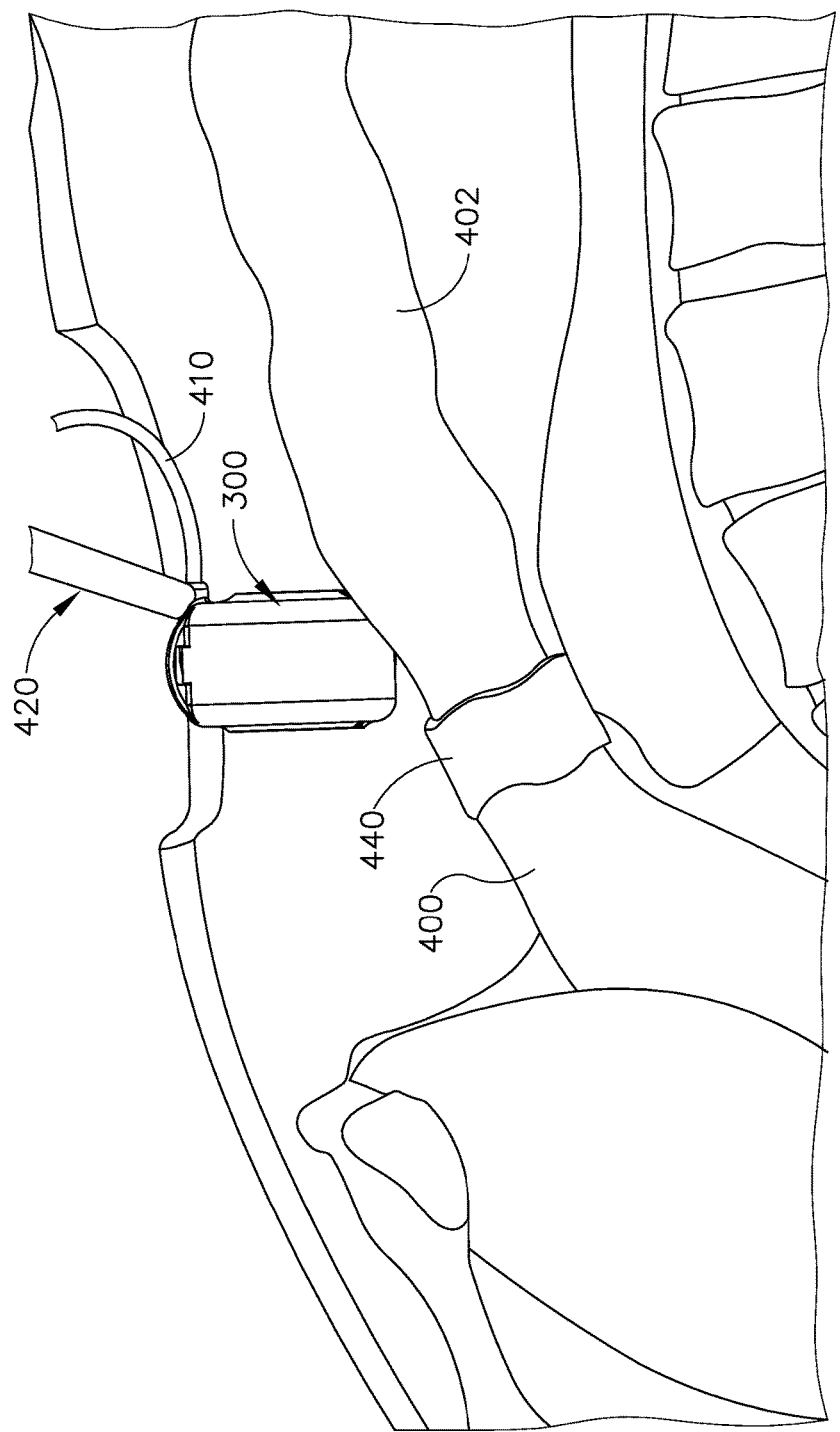
FIG. 15J depicts a perspective view of a tenth stage of the procedure of FIG. 15A.
Figure 15K:
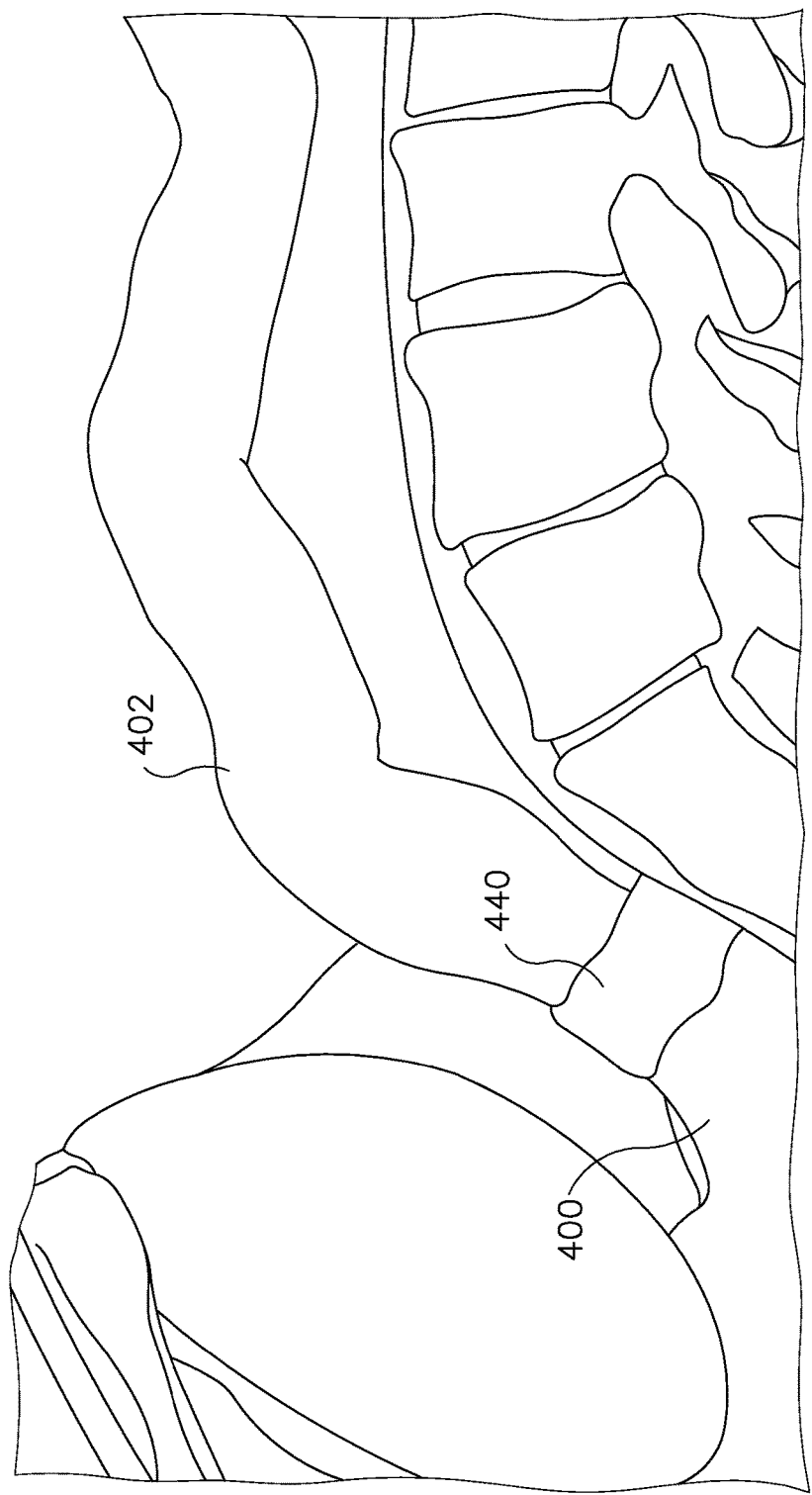
FIG. 15K depicts a perspective view of a eleventh stage of the procedure of FIG. 15A.

After fluid(s) has/have been delivered to the interior (330) of cuff (300), cuff (300) remains in place for at least a certain cure period. Various suitable cure periods will be apparent to those of ordinary skill in the art based on the selected fluid(s). After sufficient time is elapsed, the operator severs strap (320) using a conventional cutting instrument (430), as shown in FIG. 15I. Grasping instrument (420) is then used to remove cuff (300) from the anastomosis site, as shown in FIG. 15J, leaving behind a cured fluid seal (440). Cured fluid seal (440) is in the form of the interior (330) of cuff (300) and is substantially secured to the serosa layer of the tissue that it is in contact with. The joined tissue portions (400, 402) are then put back in appropriate positions as shown in FIG. 15K. Cured fluid seal (440) supplements staples (66) in providing additional structural integrity to the anastomosis and/or in providing a secondary seal to the anastomosis, further reducing any risk of leaking at the anastomosis site.

It should be understood that cuff (300) may be varied in numerous ways. By way of example only, a plurality of tissue stand-off members may project inwardly from body (302) into the interior (330) of cuff (300). Such stand-off members may push tissue away from the inner surface of body (300), ensuring that there is sufficient space within interior (330) for enough fluid to fill interior to form a cured fluid seal (440) of sufficient and substantially consistent thickness. As another merely illustrative variation, cuff (300) may be resiliently biased to assume a closed position. For instance, body (302) may be formed of a resilient material and/or one or more resilient members may be incorporated into cuff (300) to resiliently bias cuff (300) to a closed position. As yet another merely illustrative variation, magnets may be used to assist with closure of cuff (300). For instance, a magnet may be placed at or under one seam face (340, 342) while another magnet (or just a ferrous material) may be placed at or under the other seam face (342). In addition or in the alternative, a drawstring, suture, and or other feature may be used in place of strap (320) to secure cuff (300) in a closed position. Cuff (300) may also include just one port (308, 310) or more than two ports (308, 310). Furthermore, cuff (300) may include various kinds of conduits, passageways, and other fluid communication features and configurations to assist in distributing fluid within the interior (330) of cuff (300). Such conduits may extend circumferentially, longitudinally, and/or in various other directions. Other variations of cuff (300) will be apparent to those of ordinary skill in the art in view of the teachings herein.

In some instances, it may be desirable to remove instrument (10) before forming a cured fluid seal (440). It may also be desirable to test the seal of an anastomosis site after a cured fluid seal (440) has been installed. FIGS. 16A-16E show an exemplary instrument end effector (500) that may be used to provide a mandrel for forming cured fluid seal (440) and for testing the seal of an anastomosis site after a cured fluid seal (440) has been installed. End effector (500) may be disposed at the distal end of a dual lumen catheter or at the distal end of some other kind of shaft assembly. End effector (500) comprises a distal balloon (502) and a proximal balloon (504), both of which are coupled with an inflation lumen (506). End effector (500) further includes a lateral opening (510) positioned between balloons (502, 504). Lateral opening (510) is coupled with a pressurized air lumen (512). Lumens (506, 512) may both be coupled with a pressurized air source.

As shown in FIG. 16A, end effector (500) may be positioned at an anastomosis site (450) while balloons (502, 504) are both in a deflated state. As can be seen, instrument (10) has already been used to secure the anastomosis site (450) with annular arrays of staples (66) and has been removed. End effector (500) may be positioned with visualization from an endoscope or some other type of visualization device. End effector (500) is positioned such that balloon (502) is at one side of anastomosis site (450), adjacent to a first intestine section (402); while balloon (504) is at the other side of anastomosis site (450), adjacent to a second intestine section (400). Once end effector (500) is properly positioned, pressurized air is communicated via lumen (506) to inflate balloons (502, 504) as shown in FIG. 16B. Inflated balloons (502, 504) bear slightly against intestine sections (400, 402). After balloons (502, 504) have been inflated, cuff (300) is positioned about the exterior of the anastomosis site (450) and is filled with fluid, as shown in FIG. 16C. Balloons (502, 504) serve as mandrels, supporting intestine sections (400, 402) against inwardly directed forces from cuff (300) and the fluid. Cuff (300) is left in place as the fluid cures and is then removed as shown in FIG. 16D after a sufficient cure time has elapsed, leaving behind a cured fluid seal (440).

In some instances, end effector (500) is then used to test the seal integrity of cured fluid seal (440). As shown in FIG. 16E, this is done by communicating pressurized air to lumen (512) while balloons (502, 504) are still inflated. The pressurized air escapes through lateral opening (510) and is trapped between inflated balloons (502, 504). This causes the pressurized air to press outwardly on the anastomosis site (450), such that any leaks may be detected in the event that pressurized air escapes past cured fluid seal (440). While this testing example has been provided in the context of end effector (500) being used as a mandrel for cuff (300) and the curing fluid, it should be understood that end effector (500) may also be used to test the seal integrity of a cured fluid seal (440) that has been formed using the technique shown in FIGS. 15A-15K. It should also be understood that, in addition to or in lieu of being used to test the seal integrity of cured fluid seal (440), lateral opening (510) may be used to deliver fluids (e.g., sealants, nutritional supplements, etc.) to the staple line or other internal portions of the anastomosis site (450). Other suitable ways in which end effector (500) may be varied and used will be apparent to those of ordinary skill in the art in view of the teachings herein.

As yet another merely illustrative variation, a procedure may entail clamping a portion of intestine section (402) (e.g., using a conventional clamping device) and then introducing a pressurized fluid (e.g., saline, air, etc.) to the anastomosis site (450) via intestine section (400). The pressurized fluid within intestine sections (400, 402) may provide structural integrity to intestine sections (400, 402) at the anastomosis site (450), thereby providing an effective mandrel. With these regions of intestine sections (400, 402) filled with pressurized fluid, cuff (300) may be secured around the anastomosis site (450) as described above and fluid may be introduced into the interior (330) of cuff (300) to produce a cured fluid seal (440) as described above. Once the cured fluid seal (440) has been created and cuff (300) has been removed, pressure may be relieved within intestine sections (400, 402) and the clamping device may be removed from intestine section (402).

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. patent application Ser. No. 13/693,430, entitled "Trans-Oral Circular Anvil Introduction System with Dilation Feature," filed Dec. 4, 2012, published as U.S. Pat. Pub. No. 2014/0151429 on Jun. 5, 2014, the disclosure of which is incorporated by reference herein; U.S. patent application Ser. No. 13/688,951, entitled"Surgical Staple with Integral Pledget for Tip Deflection," filed Nov. 29, 2012, issued as U.S. Pat. No. 9,289,207 on Mar. 22, 2016, the disclosure of which is incorporated by reference herein; U.S. patent application Ser. No. 13/706,827, entitled "Surgical Stapler with Varying Staple Widths along Different Circumferences," filed Dec. 6, 2012, published as U.S. Pat. Pub. No. 2014/158747 on Jun. 12, 2014. the disclosure of which is incorporated by reference herein; U.S. patent application Ser. No. 13/688,992, entitled "Pivoting Anvil for Surgical Circular Stapler," filed Nov. 29, 2012, published as U.S. Pat. Pub. No. 2014/0144969 on May 29, 2014, the disclosure of which is incorporated by reference herein; U.S. patent application Ser. No. 13/693,455, entitled "Circular Anvil Introduction System with Alignment Feature," filed Dec. 4, 2012, published as U.S. Pat. Pub. No. 2014/015143 on Jun. 5, 2014, now U.S. Pat. No. 9,498,222, issued Nov. 22, 2016, the disclosure of which is incorporated by reference herein; U.S. patent application Ser. No. 13/716,313, entitled "Circular Stapler with Selectable Motorized and Manual Control, Including a Control Ring," filed Dec. 17, 2012, published as U.S. Pat. Pub. No. 2014/0166717 on Jun. 19, 2014, now U.S. Pat. No. 9,532,783, issued Jan. 3, 2017, the disclosure of which is incorporated by reference herein; U.S. patent application Ser. No. 13/716,318, entitled "Motor Driven Rotary Input Circular Stapler with Modular End Effector," filed Dec. 17, 2012, published as U.S. Pat. Pub. No. 2014/0166728 on Jun. 19, 2014, the disclosure of which is incorporated by reference herein; and/or U.S. patent application Ser. No. 13/716,323, entitled "Motor Driven Rotary Input Circular Stapler with Lockable Flexible Shaft," filed Dec. 17, 2012, published as U.S. Pat. Pub. No. 2014/0166718 on Jun. 19, 2014, now U.S. Pat. No. 9,463,022, issued Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of sealing an anastomosis site, wherein the anastomosis site is defined by the ends of two tubular anatomical structures, the method comprising:
    (a) joining the ends of the two tubular anatomical structures together with a circular stapler, such that the ends of the two tubular anatomical structures are stapled together;
    (b) placing a cuff about the ends of the two tubular anatomical structures, wherein the cuff defines an interior space between an inner surface of the cuff and the exterior of the two tubular anatomical structures, wherein the act of placing the cuff about the ends of the two tubular anatomical structures is performed while the circular stapler is positioned at the anastomosis site, such that the circular stapler provides a mandrel for the cuff and the fluid in the interior space;
    (c) introducing a fluid into the interior space;
    (d) allowing the fluid to cure in the interior space to create a cured fluid seal; and
    (e) removing the cuff, leaving behind the cured fluid seal.

2. The method of claim 1, the method further comprising:
    (a) clamping one of the tubular anatomical structures after the ends of the two tubular anatomical structures are stapled together; and
    (b) communicating a pressurized fluid to the joined tubular anatomical structures to pressurize the joined tubular anatomical structures,
    wherein the act of placing a cuff about the ends of the two tubular anatomical structures is performed while the joined tubular anatomical structures are pressurized,
    wherein the act of introducing fluid is performed while the joined tubular anatomical structures are pressurized.

3. The method of claim 1, further comprising attaching the cuff loosely about one of the tubular anatomical structures prior to the act of joining the ends of the two tubular structures together with the circular stapler.

4. The method of claim 1, further comprising communicating pressurized air to an interior region of the anastomosis site to test the cured fluid seal for leaks.

5. A method of sealing an anastomosis site, wherein the anastomosis site is defined by the ends of two tubular anatomical structures, the method comprising:
  (a) joining the ends of the two tubular anatomical structures together with a circular stapler, such that the ends of the two tubular anatomical structures are stapled together;
  (b) inflating a first balloon at a first end of the anastomosis site;
  (c) inflating a second balloon at a second end of the anastomosis site;
  (d) placing a cuff about the ends of the two tubular anatomical structures, wherein the cuff defines an interior space between an inner surface of the cuff and the exterior of the two tubular anatomical structures, wherein the cuff is positioned around regions associated with the first and second balloons;
  (e) introducing a fluid into the interior space;
  (f) allowing the fluid to cure in the interior space; and
  (g) removing the cuff, leaving behind a cured fluid seal.

* * * * *